(12) United States Patent
Wakita et al.

(10) Patent No.: US 9,541,496 B2
(45) Date of Patent: Jan. 10, 2017

(54) FRESHNESS ESTIMATION METHOD, FRESHNESS ESTIMATION APPARATUS, AND NON-VOLATILE RECORDING MEDIUM

(71) Applicant: Panasonic Corporation, Osaka (JP)

(72) Inventors: Yumi Wakita, Nara (JP); Jun Ozawa, Nara (JP); Naoshi Kondo, Kyoto (JP); Yuuichi Ogawa, Kyoto (JP); Tetsuhito Suzuki, Kyoto (JP)

(73) Assignee: Panasonic Corporation, Osaka (JP)

( * ) Notice: Subject to any disclaimer, the term of this patent is extended or adjusted under 35 U.S.C. 154(b) by 0 days.

(21) Appl. No.: 14/702,606

(22) Filed: May 1, 2015

(65) Prior Publication Data
US 2015/0330906 A1 Nov. 19, 2015

(30) Foreign Application Priority Data

May 15, 2014 (JP) .................................. 2014-101797
Jan. 26, 2015 (JP) .................................. 2015-012811

(51) Int. Cl.
| | |
|---|---|
| *G01N 21/00* | (2006.01) |
| *G01N 21/31* | (2006.01) |
| *G01J 3/42* | (2006.01) |
| *G01N 33/12* | (2006.01) |
| *G01N 21/84* | (2006.01) |

(52) U.S. Cl.
CPC .............. *G01N 21/314* (2013.01); *G01J 3/42* (2013.01); *G01N 21/31* (2013.01); *G01N 21/84* (2013.01); *G01N 33/12* (2013.01); *G01J 2003/425* (2013.01); *G01N 21/3151* (2013.01); *G01N 2021/3155* (2013.01); *G01N 2201/0635* (2013.01); *G01N 2201/129* (2013.01)

(58) Field of Classification Search
CPC ........ G01N 21/84; G01N 21/33; G01N 33/12; G01N 2201/0221; G01N 21/3563
USPC .......................... 356/432–440, 319, 320, 326
See application file for complete search history.

(56) References Cited

U.S. PATENT DOCUMENTS

| | | | | |
|---|---|---|---|---|
| 5,088,822 | A | * | 2/1992 | Kanda .................... G01N 33/12 356/326 |
| 5,599,913 | A | * | 2/1997 | Harris ................... C07C 205/42 435/808 |
| 9,316,595 | B2 | * | 4/2016 | Wakita ................... G01N 21/84 |
| 2005/0164754 | A1 | * | 7/2005 | Mikami ............... G01N 21/314 460/1 |

(Continued)

FOREIGN PATENT DOCUMENTS

| | | |
|---|---|---|
| JP | 7-213488 | 8/1995 |
| JP | 2010-268792 | 12/2010 |

OTHER PUBLICATIONS

Extended European Search Report issued Sep. 18, 2015 in European Application No. 15166718.5.

(Continued)

*Primary Examiner* — Hoa Pham
(74) *Attorney, Agent, or Firm* — Wenderoth, Lind & Ponack, L.L.P.

(57) ABSTRACT

A freshness estimation method includes obtaining an absorbance spectrum that is obtained by irradiating an eye of a fish with light having all or part of a wavelength band from 315 nm to 450 nm; and estimating freshness of the fish by using a shape of the obtained absorbance spectrum.

12 Claims, 20 Drawing Sheets

(56) References Cited

U.S. PATENT DOCUMENTS

2015/0247807 A1* 9/2015 Wakita .................. G01N 21/33
250/338.1
2015/0268211 A1* 9/2015 Wakita ............... G01N 21/4738
250/341.8

OTHER PUBLICATIONS

Hua Liu et al., "Research of Detection of Fish Freshness Based on Nis", Sensors and Transducers, Mar. 14, 2014, pp. 50-55, XP055211490.

J.M. Garrido, "Objective quality evaluation of fish by optical measurements of eye fluids (translated)", ION (Madrid) 1970, vol. 30, No. 344, Mar. 1977, p. 135, with English translation.

Yuji Nagashima et al., "Evaluation of Yellowfin Tuna Freshness by Physicochemical Properties of Eye Fluid", Journal of the Tokyo University of Fisheries, vol. 77, No. 2, Nov. 1990, pp. 153-160, XP009185969.

Anisur Rahman et al., "Discrimination Between Fresh and Spoiled Fish Using UV Spectra of Eye Fluid", Proceedings of the 7th International Symposium on Machinery and Mechatronics for Agricultural and Biosystems Engineering (ISMAB), May 21-23, 2014, Yilan, Taiwan, pp. 164-169, XP055211478.

* cited by examiner

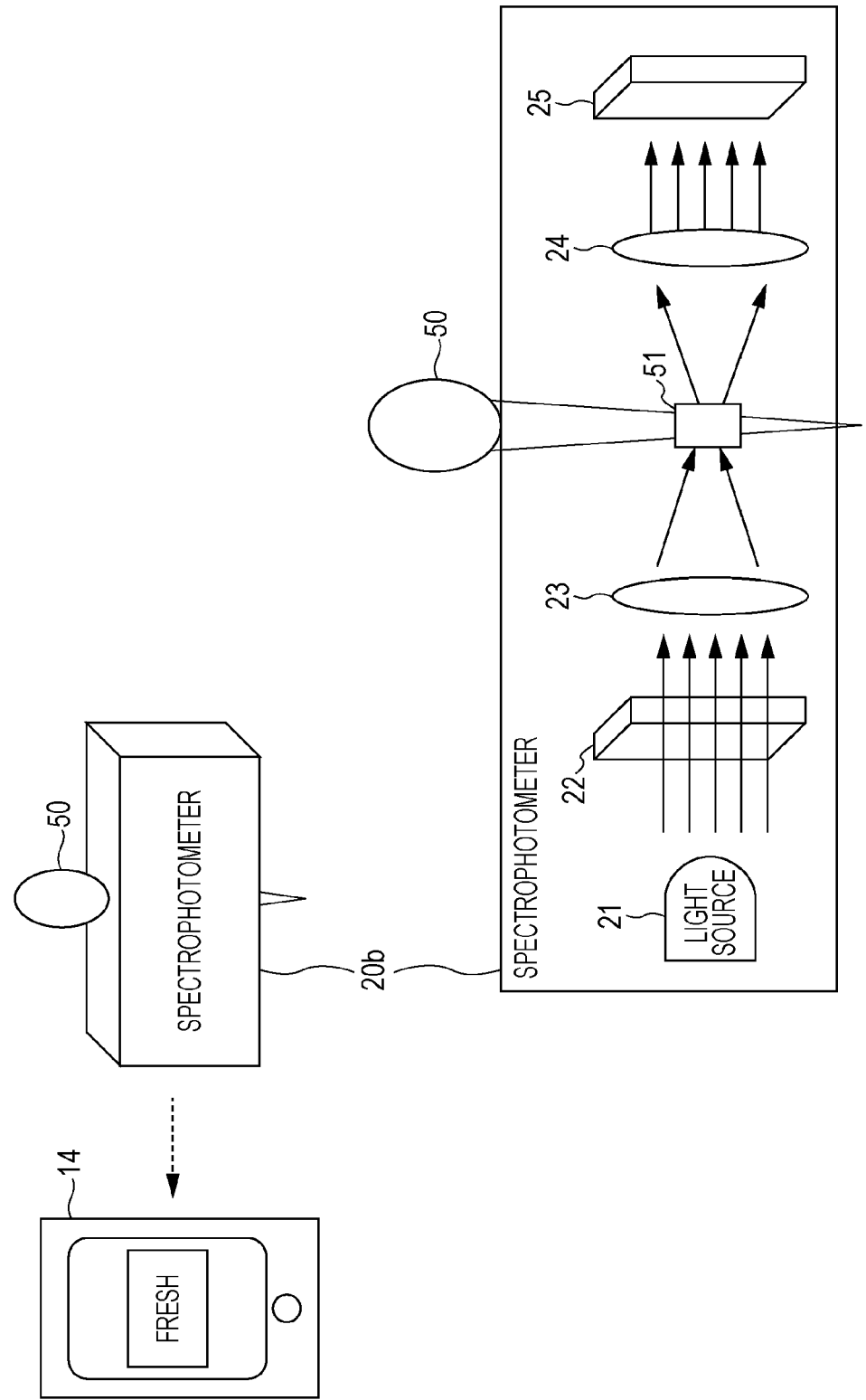

FRESHNESS ESTIMATION METHOD, FRESHNESS ESTIMATION APPARATUS, AND NON-VOLATILE RECORDING MEDIUM

BACKGROUND

1. Technical Field

The present disclosure relates to a freshness estimation method, a freshness estimation apparatus, and a non-volatile recording medium for estimating the freshness of a fish as food.

2. Description of the Related Art

Hitherto, methods for objectively estimating the freshness of a fish as food have been suggested. For example, according to Japanese Unexamined Patent Application Publication No. 7-213488, a crystalline lens of a fish is irradiated with light, and the freshness of the fish is determined by analyzing the spectrum of the reflected light. According to Japanese Unexamined Patent Application Publication No. 2010-268792, a surface of a piece of meat is irradiated with light, and the amount of bacteria on the surface is estimated by using the absorbance.

However, Japanese Unexamined Patent Application Publication No. 7-213488 does not describe a specific criterion for judgment using a spectrum, and thus the effectiveness of freshness estimation is unclear.

On the other hand, the technique disclosed in Japanese Unexamined Patent Application Publication No. 2010-268792 is effective for locally estimating the freshness of a piece of meat to be eaten, but is incapable of estimating the freshness of an entire fish.

SUMMARY

One non-limiting and exemplary embodiment provides a freshness estimation method that enables objective estimation of the freshness of an entire fish with higher accuracy.

In one general aspect, the techniques disclosed here feature a freshness estimation method including obtaining an absorbance spectrum that is obtained by irradiating an eye of a fish with light having all or part of a wavelength band from 315 nm to 450 nm; and estimating freshness of the fish by using a shape of the obtained absorbance spectrum.

According to an embodiment of the present disclosure, the freshness of an entire fish can be objectively estimated with higher accuracy.

It should be noted that general or specific embodiments may be implemented as a system, a method, an integrated circuit, a computer program, a computer-readable recording medium, or any selective combination thereof. An example of the computer-readable recording medium may be a non-volatile recording medium, such as a compact disc-read only memory (CD-ROM).

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 16 is a diagram illustrating the configuration of a spectrophotometer in the case of measuring a spectral characteristic by using the dropper-with-liquid-reservoir;

DETAILED DESCRIPTION

Figure 1:
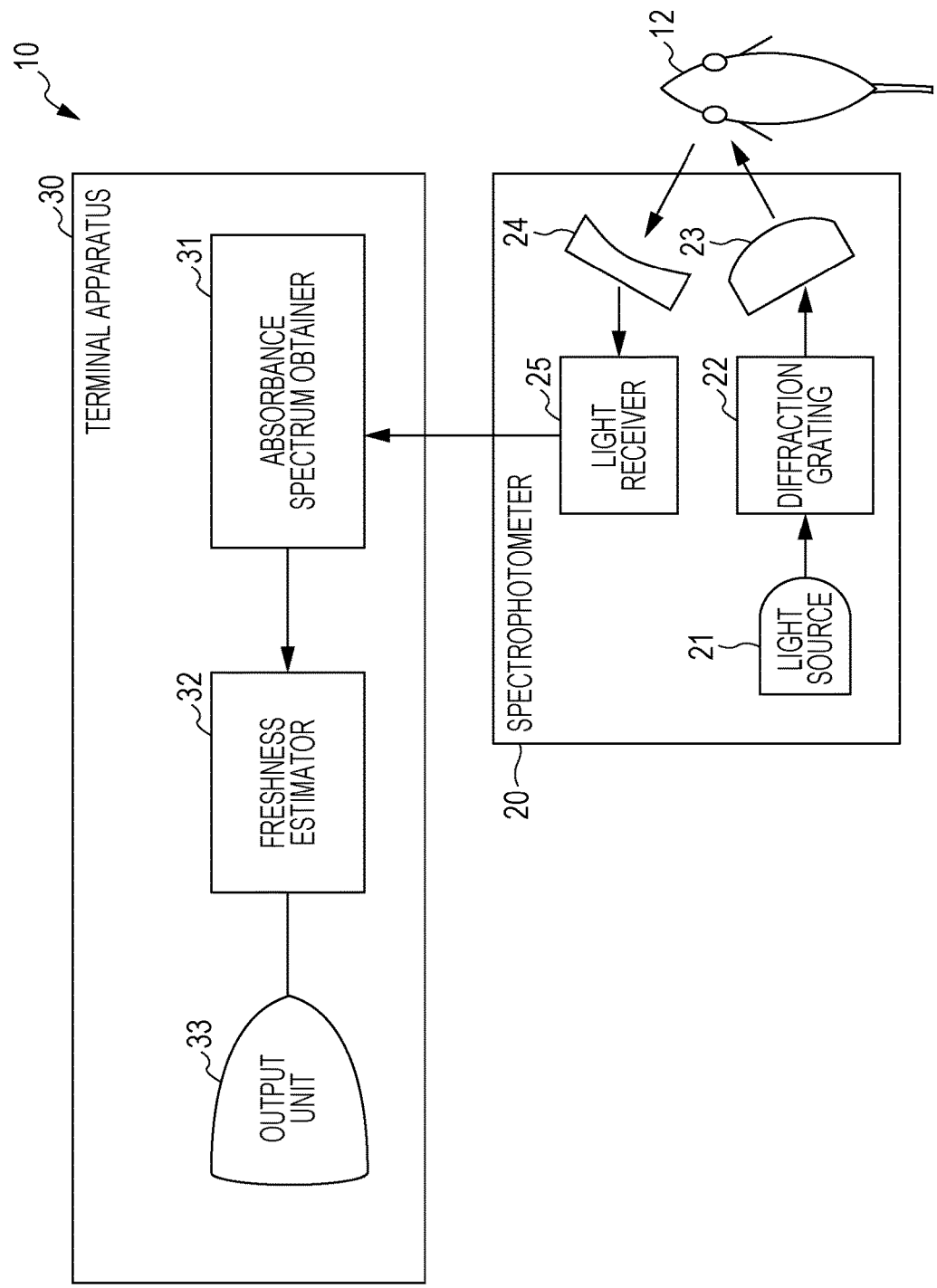
FIG. 1 is a diagram illustrating the configuration of a freshness estimation apparatus according to an embodiment of the present disclosure.

Underlying Knowledge Forming Basis of the Present Disclosure

Hitherto, a sensual method has generally been adopted to estimate the freshness of a fish, in which an experienced person visually checks the appearance of the fish and the state of the surface of the fish, and estimates the freshness on the basis of the color and complexion of the fish, the state of scales, and so forth. However, this method largely depends on the subjectivity of the experienced person, which lacks objectivity.

In recent years, an index for quantitatively assessing the freshness of a fish, called "K value", has been suggested as a method for objectively estimating the freshness of a fish. Adenosine triphosphate (ATP) in fish muscle is degraded by a related enzyme along the following degradation pathway after death of the fish. That is, adenosine triphosphate (ATP) is degraded into adenosine diphosphate (ADP), adenosine monophosphate (AMP), inosine monophosphate, (IMP), inosine (HxR), and finally into hypoxanthine (Hx). The same degradation pathway applies to all kinds of fish. By focusing on the mechanism in which ATP decreases and inosinic acid and hypoxanthine are generated as the freshness decreases, the ratio of the amount of inosinic acid and hypoxanthine to the amount of all the above-described substances is defined as a K value, and the K value is measured to quantitatively estimate the freshness of a fish.

However, in the case of measuring a K value, a chemical reaction is utilized to measure the amount of each substance. Thus, preparation for the measurement is laborious, and it takes time until a reaction is stabilized. Further, it is necessary to cut off a portion of fish meat as a sample to be used for a chemical reaction. From a hygiene viewpoint, a more non-contact and non-invasive method is desired.

Under such circumstances, methods for estimating the freshness of food in a non-contact manner in a short time have been suggested. For example, Japanese Unexamined Patent Application Publication No. 7-213488 suggests the following technique. A crystalline lens of a fish is irradiated with light, and the spectrum of the reflected light thereof is analyzed. Accordingly, a change depending on to what degree a fish eye is clouded may be detected and thereby the freshness of the fish may be estimated. On the other hand, in Japanese Unexamined Patent Application Publication No. 2010-268792, the surface of a piece of fish meat is irradiated with light, the reflectivity for light having a wavelength of 270 nm (in other words, absorbance) is measured, and thereby the amount of bacteria on the surface of the piece of fish meat is estimated. The methods described in these two publications do not utilize a chemical reaction, such as the above-described measurement of a K value, and thus enable short-time measurement. Further, these methods are non-contact measurement methods, which are advantageous from a hygiene viewpoint.

In the method according to Japanese Unexamined Patent Application Publication No. 7-213488, the freshness is estimated by detecting the attenuation of spectrum power that depends on to what degree a fish eye is clouded. However, this publication does not have a specific description about the relationship between the degree of clouding of an eye and freshness, the state of change in a spectrum, and how to detect the state of change, and the effectiveness of this method for estimating freshness is unclear.

In the method according to Japanese Unexamined Patent Application Publication No. 2010-268792, the surface of a piece of fish meat is irradiated with light, and a reflectivity (in other words, absorbance) is observed in a wavelength band around 270 nm so as to indirectly measure the amount of ATP in microorganisms existing on the surface of the piece of fish meat, and thereby the freshness is estimated. Basically, this method is advantageous for measuring an edible portion of food such as meat and vegetables. However, in the case of crustaceans and fish, it is further necessary to correlate the amount of bacteria on the surface with the amount of bacteria inside the meat, and thus it is considered that the effectiveness of this method for estimating the freshness of an entire fish is unclear.

Accordingly, the present disclosure is directed to providing a method for estimating the freshness of a fish in a non-contact and non-invasive manner in a short time, and providing a freshness estimation method and freshness estimation apparatus that enable objective estimation of the freshness of an entire fish with higher accuracy.

With earnest studies, the inventors have investigated an absorbance spectrum in a fish eye, and found that a characteristic shape appears in a wavelength band from 315 nm to 450 nm in accordance with the freshness of an entire fish (lapse of time after death). Accordingly, the inventors have acquired the knowledge that the freshness of a fish can be estimated by using such a characteristic shape of an absorbance spectrum.

A freshness estimation method according to an embodiment of the present disclosure includes obtaining an absorbance spectrum that is obtained by irradiating an eye of a fish with light having all or part of a wavelength band from 315 nm to 450 nm; and estimating freshness of the fish by using a shape of the obtained absorbance spectrum.

Accordingly, the freshness of the fish is estimated on the basis of the shape of the absorbance spectrum that is obtained by using the wavelength band (from 315 nm to 450 nm) strongly related to the freshness of the entire fish (lapse of time after death of the fish) and an irradiation target (fish eye). Thus, a method for estimating the freshness of a fish in a non-contact and non-invasive manner in a short time, that is, a freshness estimation method for a fish that enables objective estimation of the freshness of an entire fish with higher accuracy, is realized.

A freshness estimation method according to an embodiment of the present disclosure includes obtaining a plurality of absorbances that are obtained by irradiating an eye of a fish with light beams having a plurality of different wavelengths in a wavelength band from 315 nm to 450 nm; and estimating freshness of the fish by using the obtained plurality of absorbances.

Accordingly, the freshness of the fish is estimated on the basis of the absorbance (for example, the difference or ratio between absorbances) that is obtained by using light beams having a plurality of difference wavelengths in the wavelength band (from 315 nm to 450 nm) strongly related to the freshness of the entire fish (lapse of time after death of the fish) and an irradiation target (fish eye). Thus, a method for estimating the freshness of a fish in a non-contact and non-invasive manner in a short time, that is, a freshness estimation method for a fish that enables objective estimation of the freshness of an entire fish with higher accuracy, is realized.

The estimating may include estimating freshness of the fish by considering that a peak value of absorbance in a wavelength band from 410 nm to 430 nm becomes higher in a case where the fish is rotten than in a case where the fish is fresh.

Accordingly, the freshness of the fish is estimated with high accuracy by using a characteristic in which the peak value of absorbance corresponding to the wavelength band from 410 nm to 430 nm is small in a case where the fish is fresh and is large in a case where the fish is not fresh.

The estimating may include estimating that the fish is fresh in a case where a first absorbance difference is smaller than a certain threshold, the first absorbance difference being calculated by subtracting an absorbance in a certain wavelength in a wavelength band from 315 nm to 380 nm from a peak value of absorbance in a wavelength band from 410 nm to 430 nm.

Accordingly, the freshness of a fish is estimated with high accuracy by using a characteristic in which, in an absorbance spectrum of a fish eye, the first absorbance difference, which is calculated by subtracting an absorbance in a certain wavelength in a wavelength band from 315 nm to 380 nm from a peak value of absorbance in a wavelength band from 410 nm to 430 nm, is small in a case where the fish is fresh, and is large in a case where the fish is not fresh.

The estimating may include estimating that the fish is fresh in a case where a second absorbance difference is smaller than a certain threshold, the second absorbance difference being calculated by subtracting an absorbance in a certain wavelength in a wavelength band of 450 nm and more from a peak value of absorbance in a wavelength band from 410 nm to 430 nm.

Accordingly, the freshness of a fish is estimated with high accuracy by using a characteristic in which, in an absorbance spectrum of a fish eye, the second absorbance difference, which is calculated by subtracting an absorbance in a certain wavelength in a wavelength band of 450 nm and more (for example, from 450 nm to 600 nm) from a peak value of absorbance in a wavelength band from 410 nm to 430 nm, is small in a case where the fish is fresh, and is large in a case where the fish is not fresh.

The obtaining may include obtaining an absorbance spectrum that is obtained by irradiating the eye with light having a wavelength band of 450 nm and more in addition to a wavelength band from 315 nm to 380 nm. The estimating may include estimating freshness of the fish in accordance with a third absorbance difference, which is a difference between an absorbance in the wavelength band from 315 nm to 380 nm in the absorbance spectrum and an absorbance in the wavelength band of 450 nm and more in the absorbance spectrum. In this case, the estimating may include estimating that the fish is fresh in a case where the third absorbance difference is equal to or smaller than a certain threshold, and estimating that the fish is not fresh in a case where the third absorbance difference is equal to or larger than another threshold that is larger than the certain threshold.

Accordingly, the freshness of a fish is estimated with high accuracy by using a characteristic in which, in are absorbance spectrum of a fish eye, the third absorbance difference, which is calculated by subtracting an absorbance in a wavelength band of 450 nm and more (for example, from 450 nm to 600 nm) from an absorbance in a wavelength band from 315 nm to 380 nm, is small in a case where the fish is fresh, and is large in a case where the fish is not fresh.

The obtaining may include obtaining the absorbance spectrum by using a plurality of light sources that emit light beams having different wavelengths.

Accordingly, an absorbance spectrum can be easily obtained by irradiating a fish eye with light by switching the plurality of light sources, and thus a complicated optical system for sweeping the wavelength of light applied to the fish eye and separating the light into light beams of a plurality of wavelengths is not necessary.

The obtaining may include obtaining the absorbance spectrum by extracting a biological fluid in an eyeball of the fish, irradiating the extracted biological fluid with the light, and measuring light that has been transmitted through the biological fluid.

Accordingly, the freshness of a fish can be estimated with higher accuracy by obtaining an absorbance spectrum of higher accuracy by using a transmission characteristic of light in the biological fluid in the eyeball of the fish.

The obtaining may include obtaining, for classification, a plurality of absorbance spectra for a plurality of fishes including a fresh fish and a non-fresh fish, and obtaining, for freshness estimation, an absorbance spectrum for a fish as a target for which freshness is to be estimated. The estimating may include classifying the plurality of absorbance spectra obtained for classification into two classes, and determining which of the two classes includes an absorbance spectrum that is similar to the absorbance spectrum obtained for freshness estimation, and estimating freshness of the fish in accordance with a result of the determination.

Accordingly, the freshness of a fish is estimated with higher accuracy without using a complicated determination process, by using a characteristic in which absorbance spectra of a fish eye having a wavelength band from 315 nm to 450 nm are automatically clustered into two types, a fresh fish and a non-fresh fish.

A freshness estimation apparatus according to an embodiment of the present disclosure includes an absorbance spectrum obtainer that obtains an absorbance spectrum that is obtained by irradiating an eye of a fish with light having all or part of a wavelength band from 315 nm to 450 nm; and a freshness estimator that estimates freshness of the fish by using a shape of the obtained absorbance spectrum.

Accordingly, the freshness of the fish is estimated on the basis of the shape of the absorbance spectrum that is obtained by using the wavelength band (from 315 nm to 450 nm) strongly related to the freshness of the entire fish (lapse of time after death of the fish) and an irradiation target (fish eye). Thus, the freshness of a fish can be estimated in a non-contact and non-invasive manner in a short time, and the freshness of an entire fish can be objectively estimated with higher accuracy.

The freshness estimation apparatus may further include a spectrophotometer that detects an intensity of light reflected by the eye or light transmitted through the eye. The absorbance spectrum obtainer may obtain the absorbance spectrum by calculating the absorbance spectrum by using the intensity detected by the spectrophotometer.

Accordingly, an absorbance spectrum can be obtained from a target fish by using a spectrophotometer. Thus, when a fish for which the freshness is to be estimated is given, the freshness the fish can be immediately estimated.

The spectrophotometer may include a detachable dropper for sucking a biological fluid in an eyeball of the fish and for holding the biological fluid. The dropper may include a liquid reservoir that is made of quartz and that is used for storing the biological fluid that has been sucked.

Accordingly, when a fish for which the freshness is to be estimated is given, the freshness the fish can be immediately estimated by using a transmission characteristic of light in the biological fluid in the eyeball of the fish.

The freshness estimation apparatus may further include a reflection intensity measurer that includes a plurality of light sources which emit light beams having different wavelengths, that irradiates the eye with the light beams emitted from the plurality of light sources, and that detects an intensity of light reflected by the eye. The absorbance spectrum obtainer may obtain the absorbance spectrum by calculating the absorbance spectrum by using the intensity detected by the reflection intensity measurer.

Accordingly, an absorbance spectrum can be easily obtained by irradiating a fish eye with light by switching the plurality of light sources, and thus a complicated optical system for sweeping the wavelength of light applied to the fish eye and separating the light into light beams of a plurality of wavelengths is not necessary.

A freshness estimation method according to an embodiment of the present disclosure includes obtaining an absorbance that is obtained by irradiating an eye of a fish with light having one wavelength in a wavelength band from 410 nm to 430 nm; and estimating freshness of the fish by using the obtained absorbance.

Accordingly, the freshness of the fish is estimated on the basis of the absorbance that is obtained by using light having wavelengths in the wavelength band (from 410 nm to 430 nm) strongly related to the freshness of the entire fish (lapse of time after death of the fish) and an irradiation target (fish eye). Thus, a method for estimating the freshness of a fish in a non-contact and non-invasive manner in a short time, that is, a freshness estimation method for a fish that enables objective estimation of the freshness of a fish, is realized.

A freshness estimation apparatus according to an embodiment of the present disclosure includes an absorbance obtainer that obtains an absorbance that is obtained by irradiating an eye of a fish with light having one wavelength in a wavelength band from 410 nm to 430 nm; and a freshness estimator that estimates freshness of the fish by using the obtained absorbance.

Accordingly, the freshness of the fish is estimated on the basis of the absorbance that is obtained by using the wavelength band (from 410 nm to 430 nm) strongly related to the freshness of the entire fish (lapse of time after death of the fish) and an irradiation target (fish eye). Thus, the freshness of a fish can be estimated in a non-contact and non-invasive manner in a short time, and the freshness of the entire fish can be objectively estimated.

General or specific embodiments of the above-described freshness estimation method and freshness estimation apparatus may be implemented as a system, an integrated circuit, a computer program, or a computer-readable recording medium such as a CD-ROM, or any selective combination of a method, an apparatus, a system, an integrated circuit, a computer program, and a recording medium.

Hereinafter, a freshness estimation method and freshness estimation apparatus for a fish according to an embodiment of the present disclosure will be described in detail with reference to the drawings.

The embodiment and the modifications thereof described below correspond a specific example of the present disclosure. The values, shapes, materials, components, positions and connection states of the components, steps, and the order of the steps according to the following embodiment and the modifications thereof are examples, and do not limit the present disclosure. Among the components according to the following embodiment, a component that is not described in an independent claim defining the most generic concept is described as an optional component.

Embodiment

Hereinafter, an embodiment of the present disclosure will be described with reference to the attached drawings.

FIG. 1 is a diagram illustrating the configuration of a freshness estimation apparatus 10 for a fish according to the embodiment of the present disclosure. The freshness estimation apparatus 10 estimates the freshness of a fish, and includes a spectrophotometer 20 and a terminal apparatus 30. FIG. 1 also illustrates a fish 12 as a target for which the freshness is to be estimated. The fish 12 may be placed on a table (not illustrated) or the like where the position of an eye can be adjusted.

The spectrophotometer 20 is an example of a measurer that irradiates an eye of the fish 12 with light having all or part of a wavelength band from 310 nm to 450 nm and measures the spectral characteristic thereof (detects the intensity of reflected light or transmitted light), and includes a light source 21, a diffraction grating 22, a focus lens 23, a condensing lens 24, and a light receiver 25. The spectrophotometer 20 illustrated in FIG. 1 has a function of detecting reflected light.

The light source 21 is an example of a light source that emits light having all or part of the wavelength band from 310 nm to 450 nm, for example, a xenon flash lamp that emits light having wavelengths from an ultraviolet range to a visible range. The diffraction grating 22 is a spectroscope that separates light emitted from the light source 21 into monochromatic light components. The focus lens 23 collects the light components separated by the diffraction grating 22 and irradiates an eye of the fish 12 with the collected light. The condensing lens 24 collects light reflected by the eye of the fish 12 and leads the light to the light receiver 25. The light receiver 25 is a sensor that detects the intensity of the reflected light that has entered through the condensing lens 24 (converts the light into an electric signal), for example, a photomultiplier tube, a photodiode, or the like. With the spectrophotometer 20, a diffraction angle of the diffraction grating 22 is changed (swept) in response to a control signal transmitted from a driving device (not illustrated), and accordingly the eye of the fish 12 can be irradiated with light having wavelengths from the ultraviolet range to the visible range, and the intensities of reflected light in individual wavelengths (spectral characteristics) can be output.

Instead of the diffraction grating 22, a prism may be used as a spectroscope. The focus lens 23 and the condensing lens 24 are optional components, which are not always necessary or may be replaced with another optical system such as a mirror. Further, instead of being irradiated with monochromatic light, the eye of the fish 12 may be irradiated with light having all or part of the wavelength band from 310 nm to 450 nm (for example, light having wavelengths from the ultraviolet range to the visible range), and the light reflected thereby or the light transmitted therethrough may be separated and detected, so as to collectively detect the intensity of the reflected light or transmitted light in the wavelength band.

The terminal apparatus 30 performs the processing of estimating the freshness of the fish 12 by using the spectral characteristic (the intensity of the reflected light or transmitted light) obtained by the spectrophotometer 20, and includes an absorbance spectrum obtainer 31, a freshness estimator 32, and an output unit 33.

The absorbance spectrum obtainer 31 is a processor that obtains an absorbance spectrum that is obtained by irradiating the eye of the fish 12 with light having all or part of the wavelength band from 310 nm to 450 nm, and includes, in this embodiment, a communication interface that obtains a spectral characteristic (the intensity of reflected light or transmitted light) from the spectrophotometer 20 and an arithmetic processor that calculates an absorbance spectrum on the basis of the obtained spectral characteristic.

More specifically, the absorbance spectrum obtainer 31 receives the intensities of reflected light or transmitted light of individual wavelengths from the spectrophotometer 20, and then calculates absorbances for the individual wavelengths in accordance with the following equation 1, so as to calculate an absorbance spectrum.

$$A(r) = -\log(I(r)/I_0(r)) \qquad \text{equation 1}$$

Here, A (r) represents the absorbance for a wavelength r, I (r) represents the intensity of reflected light or transmitted light for the wavelength r, and $I_0$ (r) represents the intensity of incident light for the wavelength r. At the time of calculating absorbances for the individual wavelengths in accordance with equation 1, the absorbance spectrum obtainer 31 uses, as the intensity of incident light $I_0$ (r), a value held therein in advance (the intensity of incident light measured by the spectrophotometer 20 that is used).

The freshness estimator 32 is a processor that estimates the freshness of the fish 12 by using the shape of the absorbance spectrum obtained by the absorbance spectrum obtainer 31, and is constituted by an arithmetic processor or the like. A specific example of estimation will be described below.

The output unit 33 is a processor that outputs a result of estimation performed by the freshness estimator 32, and is, for example, a liquid crystal display or the like that displays information indicating whether or not the fish 12 is fresh. The output unit 33 may display an estimation result by using figure data, color data, and so forth as well as text data. Alternatively, the output unit 33 may output an estimation result through output of sound or output of data to the outside, instead of or in addition to display output.

The absorbance spectrum obtainer 31 and the freshness estimator 32 may be constituted by a dedicated electronic circuit or the like in a hardware manner, or may be constituted by a processor that executes a program in a software manner. In a case where the absorbance spectrum obtainer 31 and the freshness estimator 32 are constituted in a software manner, the absorbance spectrum obtainer 31 and the freshness estimator 32 are constituted by a computer including a nonvolatile memory storing a program, a volatile memory serving as a working area of a processor, the processor that executes the program, and an input/output interface that transmits a signal to and receives a signal from a peripheral circuit under control by the processor.

Figure 2:
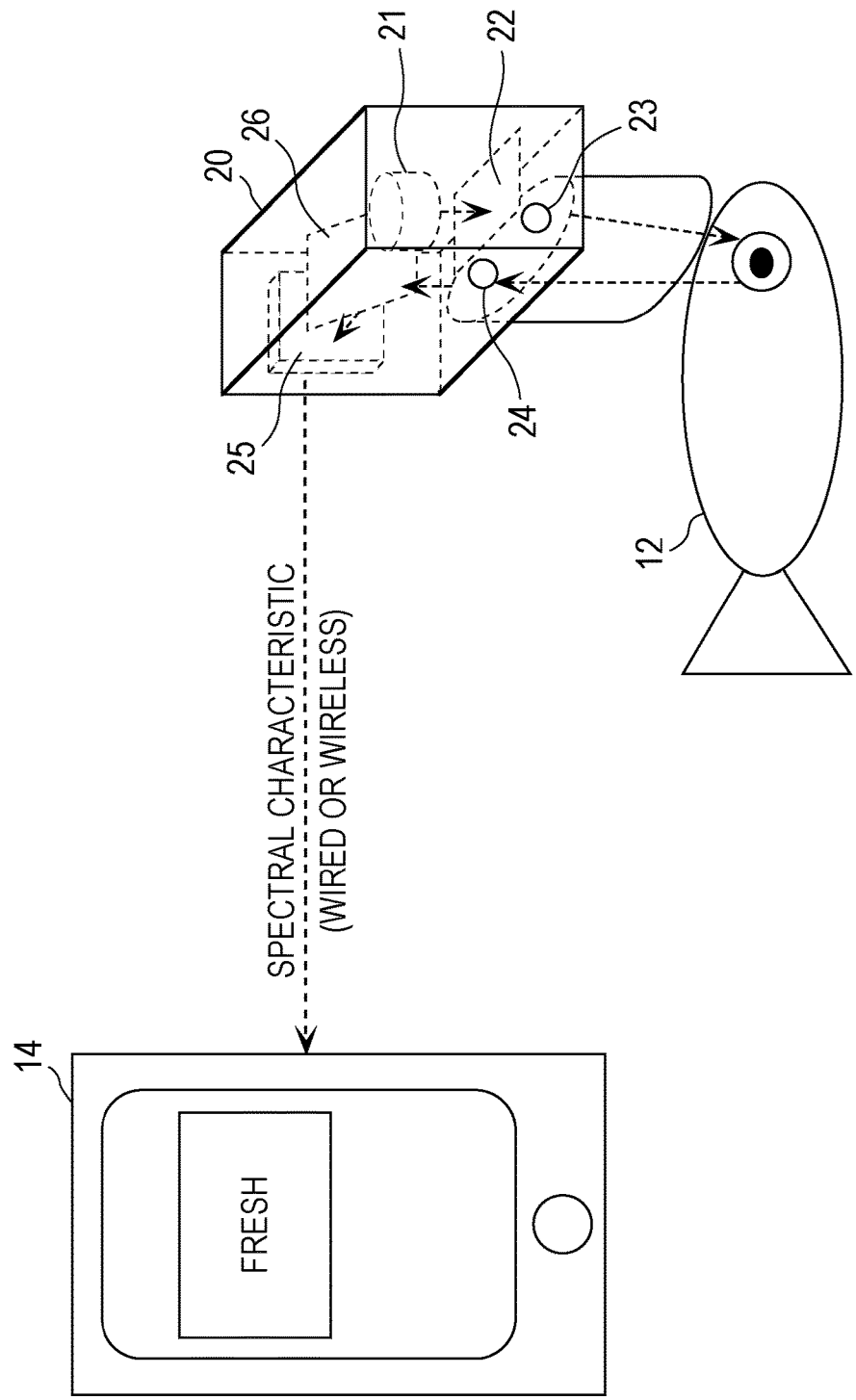
FIG. 2 is a diagram illustrating a specific example of the freshness estimation apparatus according to the embodiment of the present disclosure.

FIG. 2 is a diagram illustrating a specific example of the freshness estimation apparatus 10 illustrated in FIG. 1. Here, a smartphone (multifunction mobile phone) 14 is adopted as the terminal apparatus 30 illustrated in FIG. 1. The absorbance spectrum obtainer 31 and the freshness estimator 32 are constituted by an application program executed by the smartphone 14. The absorbance spectrum obtainer 31 obtains, from the spectrophotometer 20 via a wired or wireless communication interface, the intensities of light reflected by the eye of the fish 12 or transmitted through the eye of the fish 12 for individual wavelengths. The spectrophotometer 20 illustrated in FIG. 2 includes a reflection plate 26 that leads light passed through the condensing lens 24 to the light receiver 25, and is thereby compact in size. With use of the smartphone 14 and the compact spectrophotometer 20 illustrated in FIG. 2, the freshness of a fish can be objectively determined through a simple operation at a fish store or at home.

In the freshness estimation apparatus 10 according to the embodiment of the present disclosure, the spectrophotometer 20 is not an essential element. In a case where an absorbance spectrum that has been calculated by using a spectrophotometer or the like is generated in advance, the absorbance spectrum obtainer 31 may obtain such an absorbance spectrum generated in advance. For example, the absorbance spectrum obtainer 31 may obtain an absorbance spectrum by reading the absorbance spectrum stored in an auxiliary storage device connected to the terminal apparatus 30.

Also, in the freshness estimation apparatus 10 according to the embodiment of the present disclosure, the output unit 33 is not an essential element. Regarding an estimation result generated by the freshness estimator 32, an external apparatus connected to the terminal apparatus 30 may read and use the estimation result.

Figure 3:
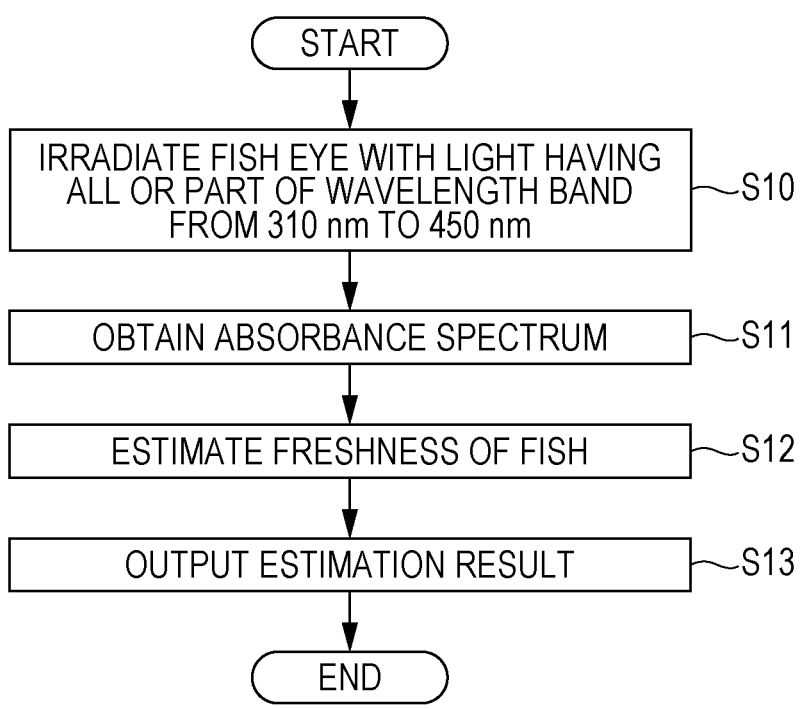
FIG. 3 is a flowchart illustrating a basic operation of the freshness estimation apparatus according to the embodiment of the present disclosure.

FIG. 3 is a flowchart illustrating a basic operation of the freshness estimation apparatus 10 (that is, a freshness estimation method for a fish) according to the embodiment having the above-described configuration.

First, the spectrophotometer 20 irradiates an eye of the fish 12 with light having all or part of the wavelength band from 310 nm to 450 nm (measurement step S10).

The absorbance spectrum obtainer 31 obtains, from the spectrophotometer 20, the intensities of reflected light or transmitted light for individual wavelengths, obtained through the irradiation in the measurement step S10, calculates an absorbance spectrum, and thereby obtains the absorbance spectrum (absorbance spectrum obtaining step S11).

Subsequently, the freshness estimator 32 estimates the freshness of the fish 12 by using the shape of the absorbance spectrum obtained by the absorbance spectrum obtainer 31 (freshness estimation step S12). A specific estimation method will be described below.

Finally, the output unit 33 outputs the estimation result generated by the freshness estimator 32 by, for example, displaying it (output step S13).

In the freshness estimation method for a fish according to the embodiment of the present disclosure, the measurement step S10 performed by using the spectrophotometer 20 is not essential. For example, the absorbance spectrum obtainer 31 may obtain an absorbance spectrum by reading the absorbance spectrum stored in the auxiliary storage device connected to the terminal apparatus 30.

Also, in the freshness estimation method for a fish according to the embodiment of the present disclosure, the output step S13 performed by using the output unit 33 is not essential. For example, an estimation result generated by the freshness estimator 32 may be read by an external apparatus connected to the terminal apparatus 30 and may be used.

First Example of Estimating Freshness

Next, as a first example of estimating freshness by using the freshness estimation apparatus 10 according to this embodiment, a description will be given of a method for estimating the freshness of a fish by considering that a peak of an absorbance spectrum in a wavelength band from 410 nm to 430 nm increases as time elapses since death of the fish.

Figure 4:
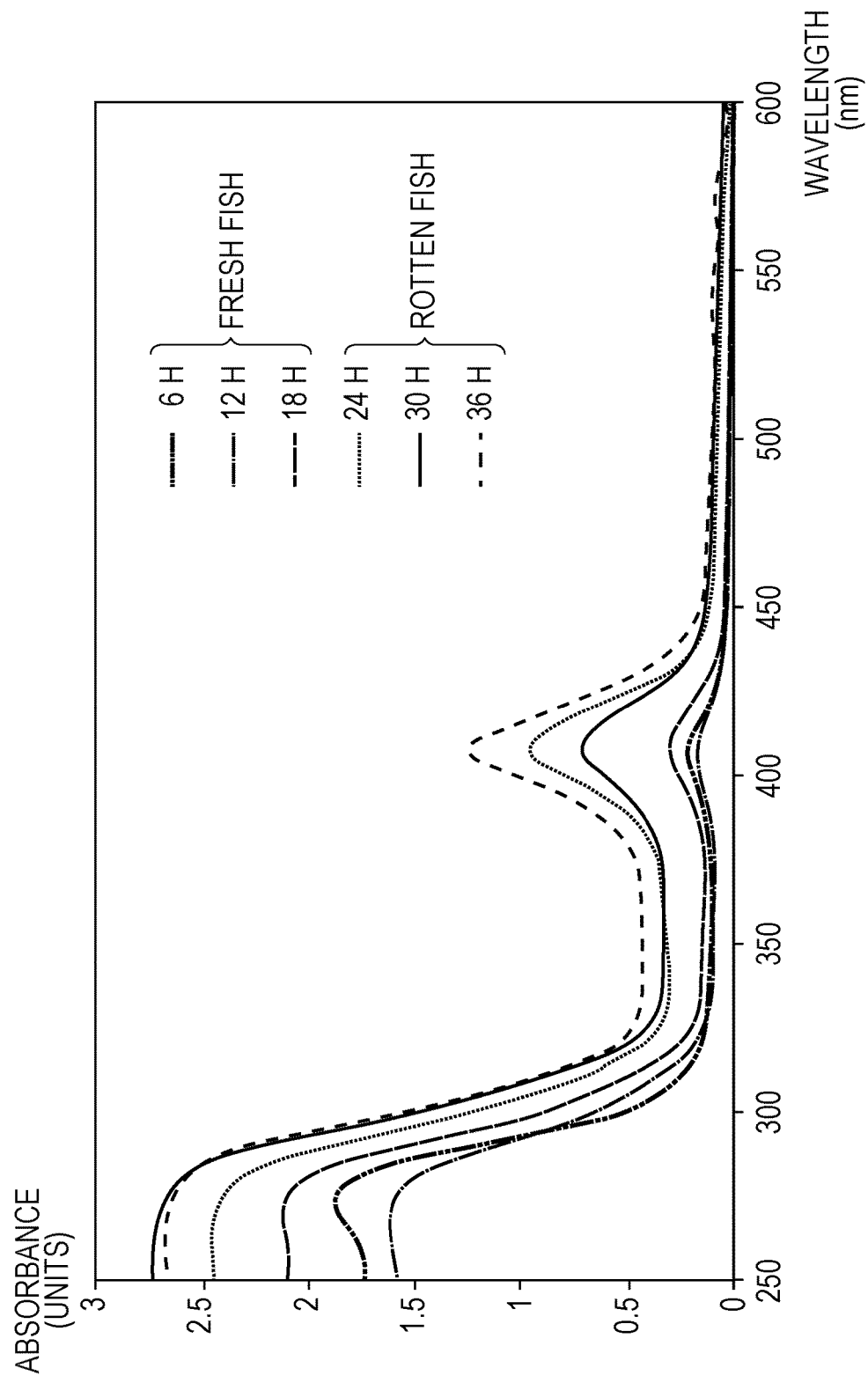
FIG. 4 is a graph illustrating absorbance spectra used in an example of estimating freshness.

FIG. 4 is a graph illustrating absorbance spectra used in the first example of estimating freshness (a wavelength band from 250 nm to 600 nm). The vertical axis of absorbance spectra illustrated in FIG. 4 (absorbance: units) represents an absorbance (calculated by subtracting, from 1, the ratio of the intensity of incident light to the intensity of transmitted light (or reflected light)) by using a logarithmic axis. Here, the graph illustrates actually measured absorbance spectra of a gel-like liquid existing between a cornea and a crystalline lens of an eye of a Japanese dace (hereinafter the liquid is referred to as a "biological fluid"). The Japanese dace is a fish categorized into Leuciscinae, Cyprinidae, Cypriniformes. Here, the graph illustrates absorbance spectra observed every 6 hours from death of the Japanese dace until 36 hours later (6, 12, 18, 24, 30, and 36 hours). In this experiment, only the biological fluid in an eyeball is extracted from an eye of the Japanese dace every 6 hours by using a syringe, the extracted biological fluid is centrifugalized for 30 minutes at a rotation speed of 5000 rpm, a supernatant liquor obtained thereby is poured into a cell having a size of 1 mm×1 cm, the supernatant liquor is irradiated with light having wavelengths of 250 nm to 600 nm by using the spectrophotometer 20, and an absorbance spectrum is calculated on the basis of the intensity of light transmitted through the supernatant liquor. It is estimated that a similar result will be obtained in a case where the fish eye is irradiated with light and an absorbance spectrum is calculated on the basis of the intensity of light reflected thereby.

As can be understood from this experiment result, in the absorbance spectra of a fresh Japanese dace (that has been dead for no longer than 18 hours after which the Japanese dace is estimated to go bad), the peak is low in the range from 410 nm to 430 nm. However, in the absorbance spectra of the Japanese dace that has been dead for 24 hours or more, the peak is high in the range from 410 nm to 430 nm. Thus, the difference or ratio between absorbance in the range from 410 nm to 430 nm and the absorbance in another stable wavelength band (where change in absorbance caused by change in wavelength is small, for example, a wavelength band from 315 nm to 380 nm) is calculated, the value obtained through the calculation is compared with a certain value (threshold), and thereby it can be determined whether the fish is fresh or rotten on the basis of the comparison result. For example, it may be determined that the fish is fresh if the difference between a peak value (for example, a maximum value) of absorbance in the wavelength band from 410 nm to 430 nm where the peak of the absorbance spectrum exists and a maximum value of absorbance in the wavelength band from 315 nm to 380 nm is smaller than a threshold (for example, 0.2), whereas it may be determined that the fish is not fresh (is rotten) if the difference is equal to or larger than the threshold.

The reason for determining whether or not the Japanese dace has been dead for more than 18 hours to determine whether or not it is fresh is as follows.

Figure 5:
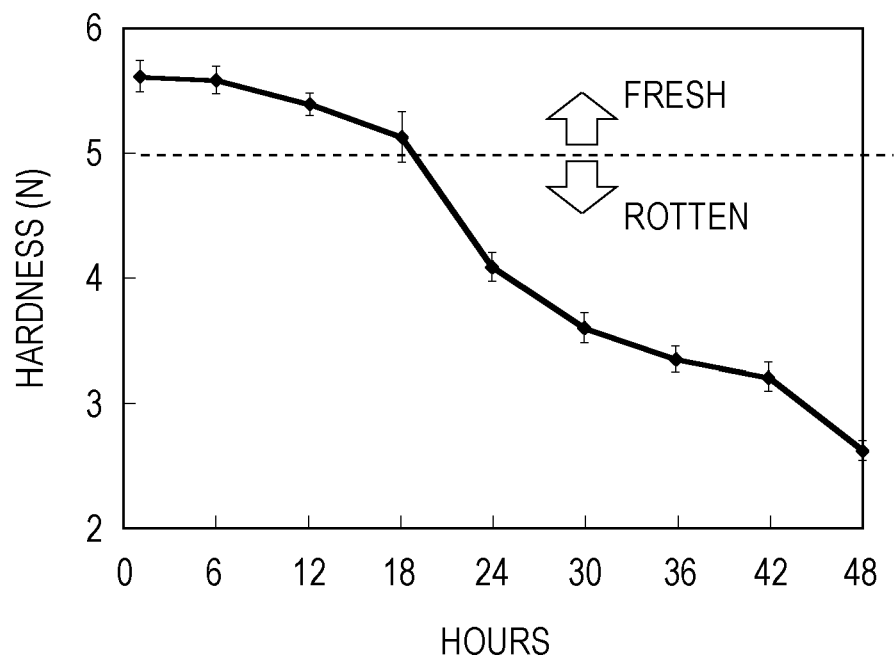
FIG. 5 is a graph illustrating an experiment result showing the relationship between lapse of time after death of a Japanese dace and a hardness index indicating rottenness.

FIG. 5 illustrates an experiment result indicating the relationship between lapse of time after death of a Japanese dace that is left under a room temperature of 20° C. (horizontal axis) and a hardness index (vertical axis: hardness (N)) indicating a rotten state. In this experiment, a hardness tester was used. The hardness tester is a tool for measuring the hardness (hardness index) of a fish on the basis of elasticity, which is measured by pushing a conical tip against fish muscle. The unit of hardness (hardness index) measured by using the hardness tester is newton (N). According to "Freshness assessment of cultured sea bream by chemical, physical and sensory methods" C Alasalver etc. Food chemistry 72 (2001) pp. 33-40, compared with the above-described K value, which is a general freshness index, the hardness index corresponding to a situation where it is determined using a K value that the fish is rotten is about 5N.

In FIG. 5, average values of hardness indices at three points of muscle at a center portion of a fish body are plotted. Fish muscle becomes harder as time elapses since death, and thus the hardness index (N) decreases. The time when the hardness index has a value of 5N, at which it is considered that the fish is rotten from an experience standpoint, was 18 hours after death. Thus, it is considered that the time when a Japanese dace goes bad in a room temperature is around 18 hours after death. On the basis of this experiment result, it was determined that a Japanese dace that has been dead for no longer than 18 hours is fresh, and that a Japanese dace that has been dead for more than 18 hours is not fresh.

Figure 6:
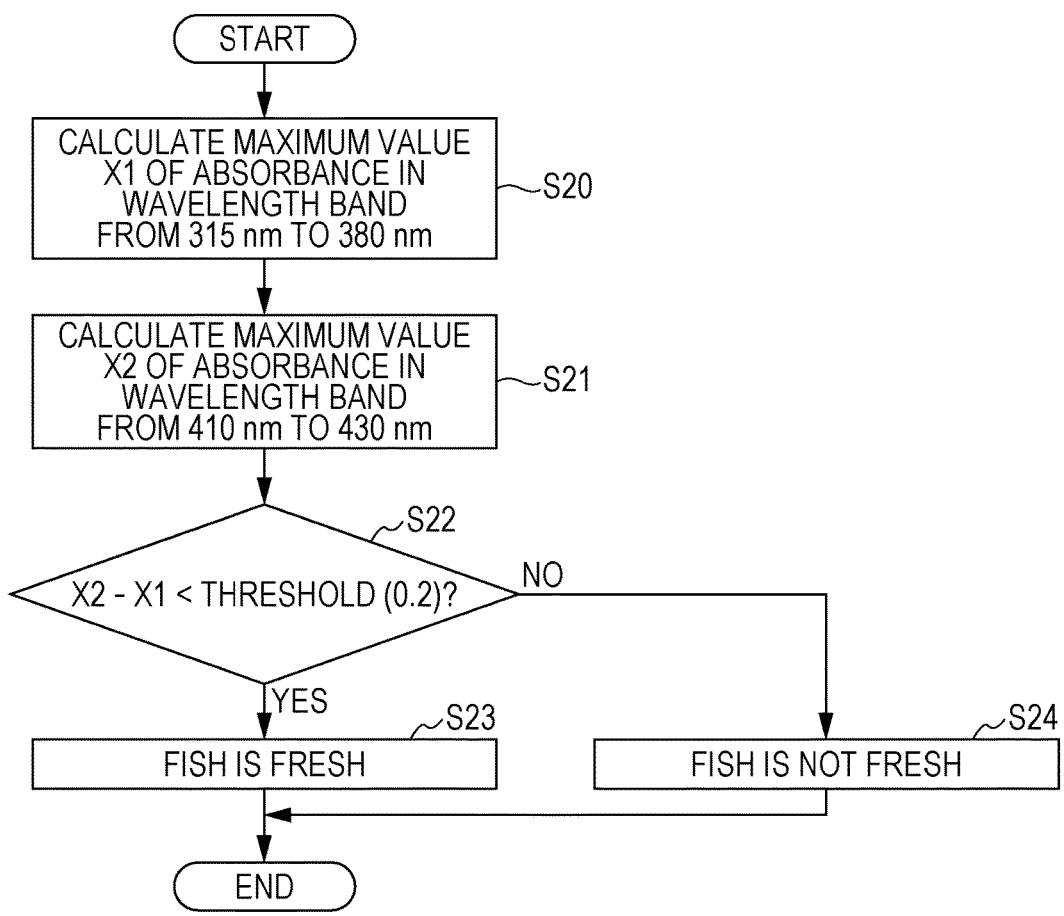
FIG. 6 is a flowchart illustrating an operation of a freshness estimator according to a first example of estimating freshness.

The above-described operation for estimating the freshness of a fish performed by the freshness estimation apparatus 10 is illustrated in the flowchart in FIG. 6. FIG. 6 is a flowchart illustrating the operation of the freshness estimator 32 according to the first example of estimating freshness (that is, a freshness estimation method for a fish).

The freshness estimator 32 calculates a maximum value $X1$ of absorbance in the wavelength band from 315 nm to 380 nm in an absorbance spectrum (S20). Also, the freshness estimator 32 calculates a maximum value $X2$ as a peak value of absorbance in the wavelength band from 410 nm to 430 nm in the absorbance spectrum (S21).

Subsequently, the freshness estimator 32 compares a first absorbance difference, which is the difference between the two maximum values, with a threshold, which is 0.2, for example (S22). If the difference is smaller than the threshold (YES in S22), the freshness estimator 32 determines (estimates) that the fish is fresh (S23). On the other hand, if the difference is equal to or larger than the threshold (NO in S22), the freshness estimator 32 determines (estimates) that the fish is not fresh (S24). The first absorbance difference is a value obtained by subtracting a value (for example, a maximum value) of absorbance in the wavelength band from 315 nm to 380 nm from a peak value (for example, a maximum value) of absorbance in the wavelength band from 410 nm to 430 nm.

As described above, in the freshness estimation apparatus 10 and the freshness estimation method according to this embodiment, the absorbance spectrum obtainer 31 obtains an absorbance spectrum that is obtained by irradiating a fish eye with light having all or part of the wavelength band from 315 nm to 450 nm. The freshness estimator 32 calculates the difference or ratio between the absorbance in the wavelength band from 410 nm to 430 nm and the absorbance in another stable wavelength band from 315 nm to 380 nm, and determines that the fish is fresh if the value of the difference or ratio is smaller than a certain value (threshold) and determined that the fish is rotten if the value is equal to or larger than the threshold. The absorbance in the wavelength band from 410 nm to 430 nm may be a maximum value of absorbance in the wavelength band, and the absorbance in another stable wavelength band from 315 nm to 380 nm may be a maximum value of absorbance in the wavelength band. A minimum value or an average value in the wavelength band may be used instead of the maximum value.

Accordingly, the freshness of the fish is estimated on the basis of the shape of an absorbance spectrum that is obtained by using the wavelength band (315 nm to 450 nm) strongly related to the freshness of the entire fish (lapse of time after death) and the irradiation target (fish eye). Thus, the freshness of the fish can be estimated in a short time in a non-contact and non-invasive manner, and the freshness of the entire fish is objectively estimated with higher accuracy.

Figure 7:
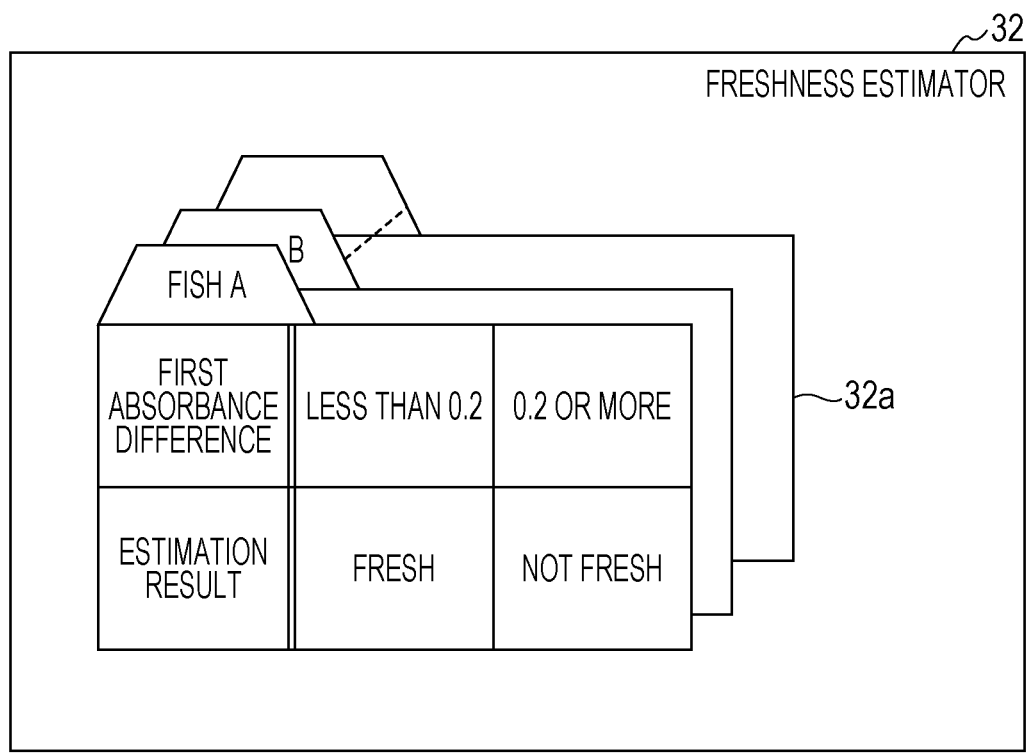
FIG. 7 is a diagram illustrating an example of a threshold table used in the first example of estimating freshness.

In the above-described first example of estimating freshness, the freshness of a fish is estimated by using one type of threshold (first threshold), but a plurality of thresholds may be used. For example, absorbance spectra as those illustrated in FIG. 4 may be obtained for individual types and individual preservation states of fishes, thresholds for a difference or ratio regarding the absorbance in the above-described individual wavelength bands (410 to 430 nm, 315 to 380 nm) for distinguishing a fresh fish from a non-fresh fish may be set, and the thresholds may be registered in a threshold table 32a illustrated in FIG. 7 so as to be stored in the freshness estimator 32. Upon receipt of input of information representing the type of fish as a target for which the freshness is to be estimated and the preservation state of the fish from a user, the freshness estimator 32 refers to the threshold table 32a in order to read the threshold corresponding to the received information representing the type and preservation state of the fish, and estimates the freshness of the fish by using the read threshold. Accordingly, highly-accurate freshness estimation can be performed in consideration of the type and preservation state of the fish.

Figure 8:
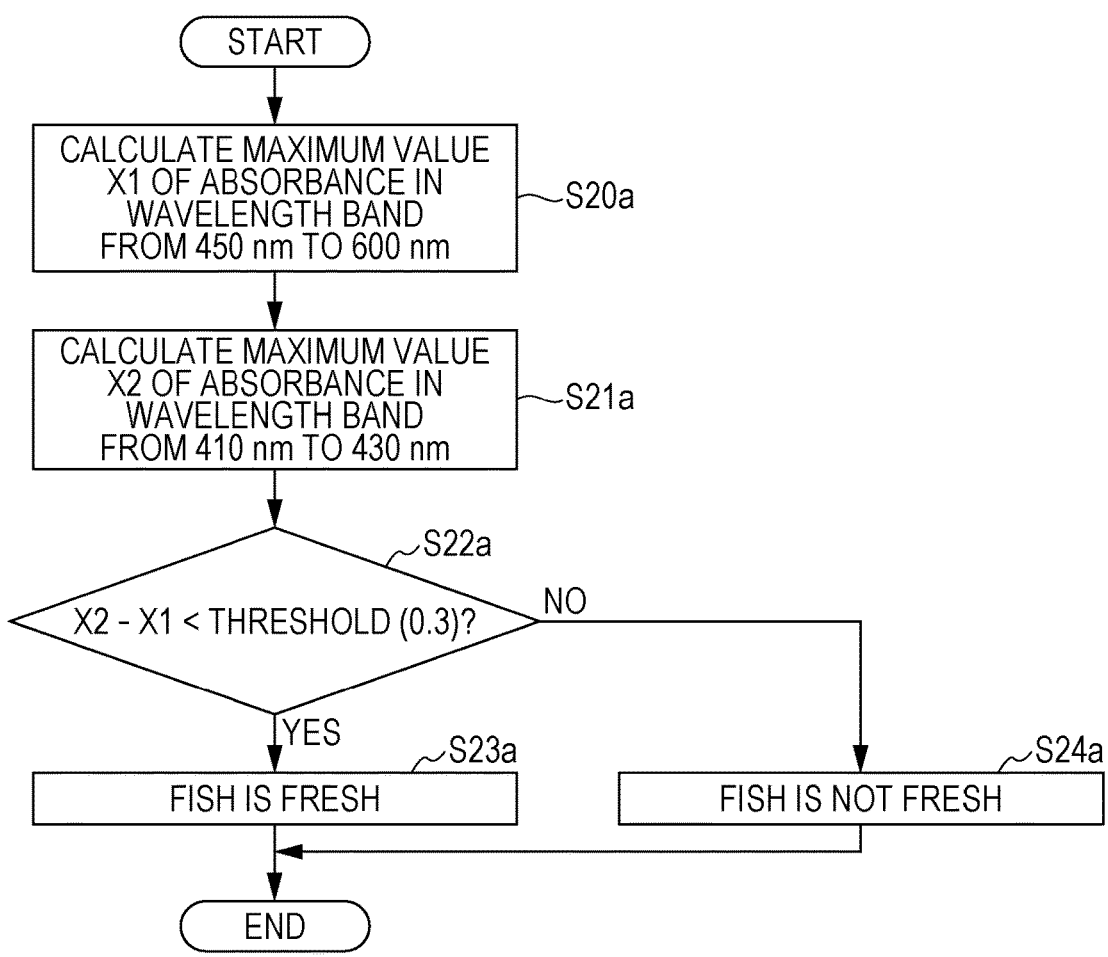
FIG. 8 is a flowchart illustrating another operation of the freshness estimator according to the first example of estimating freshness.
Figure 9:
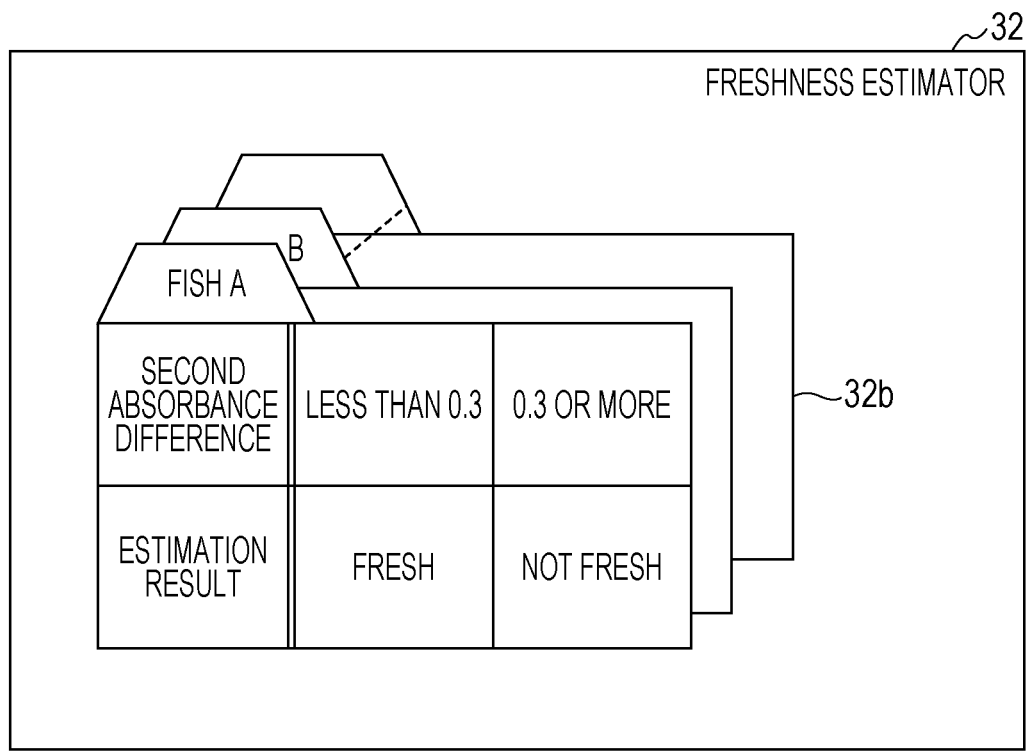
FIG. 9 is a diagram illustrating another example of a threshold table used in the first example of estimating freshness.

An example of a stable wavelength band (with slight changes in absorbance caused by change in wavelength) other than the wavelength band from 410 nm to 430 nm where the peak of a spectrum exists includes, in addition to the above-described wavelength band from 315 nm to 380 nm, a wavelength band of 450 nm and more (for example, from 450 nm to 600 nm). Thus, the freshness of a fish may be estimated on the basis of the difference or ratio between the absorbance in the wavelength band from 410 nm to 430 nm and the absorbance in the wavelength band of 450 nm and more (for example, from 450 nm to 600 nm). Alternatively, whether or not a fish is fresh may be determined on the basis of a result of comparison between the difference or ratio and a predetermined threshold. It can be estimated that stability is obtained also in the wavelength band of 600 nm or more (for example, up to 1000 nm in the infrared range beyond the visible range) in the wavelength band of 450 nm and more. An example of operation using the absorbance in the wavelength band of 450 nm and more is illustrated in the flowchart in FIG. 8. FIG. 8 is a flowchart illustrating another operation example of the freshness estimator 32 according to the first example of estimating freshness. As illustrated in FIG. 8, the freshness estimator 32 calculates a maximum value X1 of absorbance in the wavelength band of 450 nm and more (for example, from 450 nm to 600 nm) in an absorbance spectrum (S20a). Also, the freshness estimator 32 calculates a maximum value X2 of absorbance in the wavelength band of 410 nm to 430 nm in the absorbance spectrum (S21a). Subsequently, the freshness estimator 32 compares a second absorbance difference, which is the difference between the two maximum values, with a threshold, which is 0.3, for example (S22a). If the difference is smaller than the threshold (YES in S22a), the freshness estimator 32 determines (estimates) that the fish is fresh (S23a). If the difference is equal to or larger than the threshold (NO in S22a), the freshness estimator 32 determines (estimates) that the fish is not fresh (S24a). The second absorbance difference in this case is a value obtained by subtracting the value of absorbance in the wavelength band of 450 nm and more (for example, the maximum value in the wavelength band from 450 nm to 600 nm) from the peak value (for example, the maximum value) of absorbance in the wavelength band from 410 nm to 430 nm. The threshold table held by the freshness estimator 32 in this case is, for example, the threshold table 32b illustrated in FIG. 9.

Second Example of Estimating Freshness

Next, a description will be given of a second example of estimating freshness by the freshness estimation apparatus 10 according to this embodiment, that is, a method for estimating the freshness of a fish on the basis of a third absorbance difference, which is the difference between the absorbance in the wavelength band from 315 nm to 380 nm in an absorbance spectrum and the absorbance in the wavelength band of 450 nm and more (for example, from 450 nm to 600 nm).

Regarding the absorbance spectra illustrated in FIG. 4, as can be understood by comparing the spectra of 18 hours or less corresponding to the period over which the fish is not rotten (is fresh) with the spectra of 24 hours or more beyond 18 hours when it is estimated that the fish goes bad, the absorbance is higher after the fish has been rotten. In particular, it is understood that the absorbance in the wavelength band from 315 nm to 380 nm in the ultraviolet range has a large difference between before and after the fish is rotten, compared with the wavelength band of 450 nm and more.

On the basis of the above-described knowledge, in the second example of estimating freshness, the absorbance spectrum obtainer 31 obtains an absorbance spectrum that is obtained by irradiating an eye of a fish with light having a wavelength band of 450 nm and more (for example, from 450 nm to 600 nm), in addition to the wavelength band from 315 nm to 380 nm. The freshness estimator 32 estimates the freshness of the fish on the basis of a third absorbance difference, which is a difference between an absorbance in the wavelength band from 315 nm to 380 nm in an absorbance spectrum and an absorbance in the wavelength band of 450 nm and more (for example, from 450 nm to 600 nm). More specifically, the freshness estimator 32 estimates that the fish is fresh if the third absorbance difference is equal to or smaller than a certain threshold (threshold A) and that the fish is not fresh if the third absorbance difference is equal to or larger than another threshold (threshold B) larger than the certain threshold.

Figure 10:
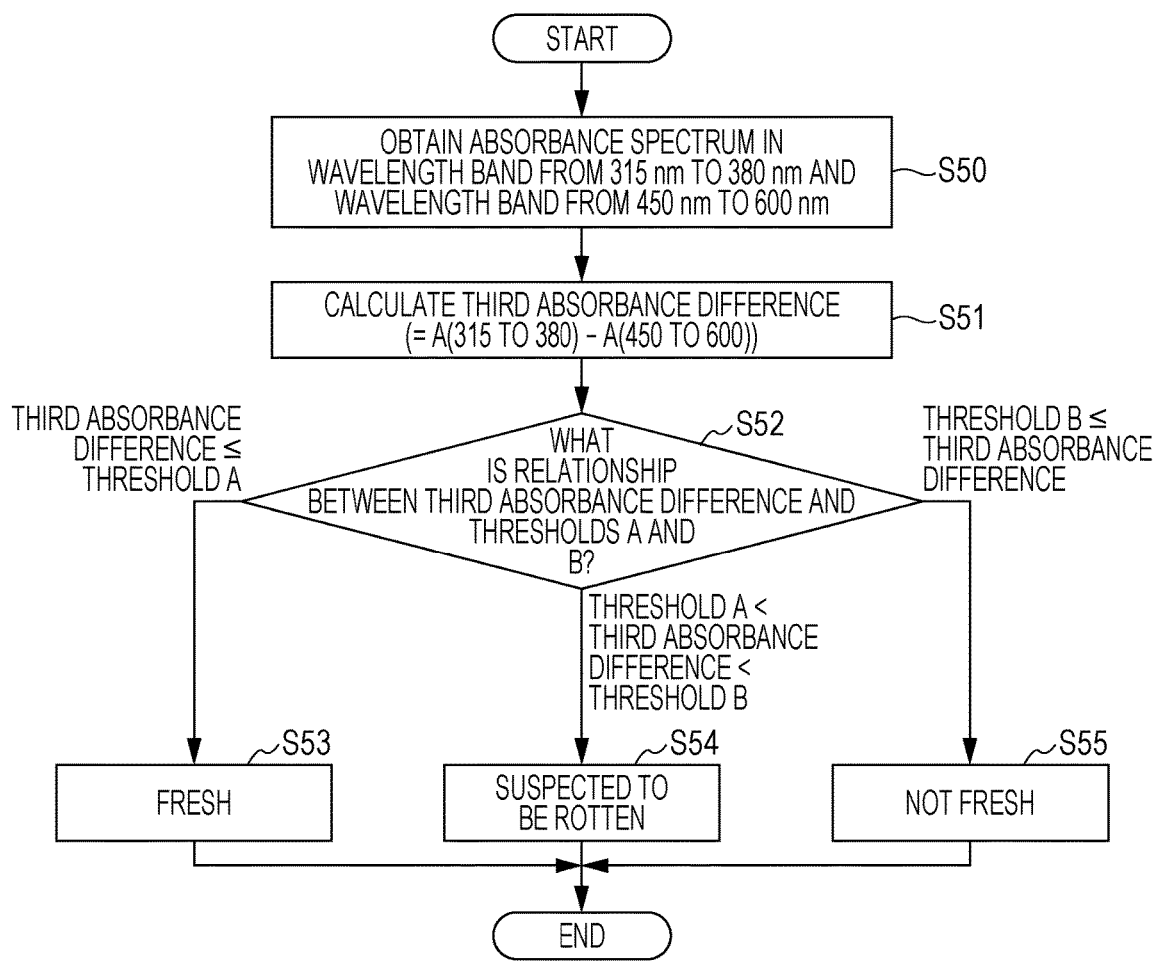
FIG. 10 is a flowchart illustrating an operation of a terminal apparatus according to a second example of estimating freshness.

More detailed description will be given below with reference to the flowchart in FIG. 10. FIG. 10 is a flowchart illustrating an example of the operation of the terminal apparatus 30 according to the second example of estimating freshness (that is, a freshness estimation method for a fish). First, the absorbance spectrum obtainer 31 obtains an absorbance spectrum that is obtained by irradiating an eye of a fish with light having the wavelength band from 450 nm to 600 nm, in addition to the wavelength band from 315 nm to 380 nm (S50).

Subsequently, the freshness estimator 32 subtracts an absorbance A (450-600) in the wavelength band of 450 nm and more (for example, 450 nm to 600 nm) from an absorbance A (315-380) in the wavelength band from 315 nm to 380 nm in an absorbance spectrum, and thereby calculates a third absorbance difference, which is the difference between both the absorbances A (S51).

Further, the freshness estimator 32 compares the third absorbance difference with the threshold A (for example, 0.2) and the threshold B (for example, 0.25) (S52). As a result, the freshness estimator 32 estimates that the fish is fresh if the third absorbance difference is equal to smaller than the threshold A (third absorbance difference threshold A) (S53), that the fish is suspected to be rotten if the third absorbance difference is larger than the threshold A and is smaller than the threshold B (threshold A<third absorbance difference<threshold B) (S54), and that the fish is not fresh if the third absorbance difference is equal to or larger than the threshold B (threshold B≤third absorbance difference) (S55).

As described above, in the second example of estimating freshness, the freshness estimator 32 estimates that the fish is fresh if the third absorbance difference, which is the difference between the absorbance in the wavelength band from 315 nm to 380 nm in an absorbance spectrum and the absorbance in the wavelength band of 450 nm and more (for example, from 450 nm to 600 nm), is equal to or smaller than the threshold A, and that the fish is not fresh if the third absorbance difference is equal to or larger than the threshold B.

Accordingly, the freshness of the fish can be estimated with high accuracy by using the characteristic in which, in an absorbance spectrum of a fish eye, the third absorbance difference, which is the difference between the absorbance in the wavelength band from 315 nm to 380 nm and the absorbance in the wavelength band of 450 nm and more (for example, from 450 nm to 600 nm), has a small value if the fish is fresh, and has a large value if the fish is not fresh.

Figure 11:
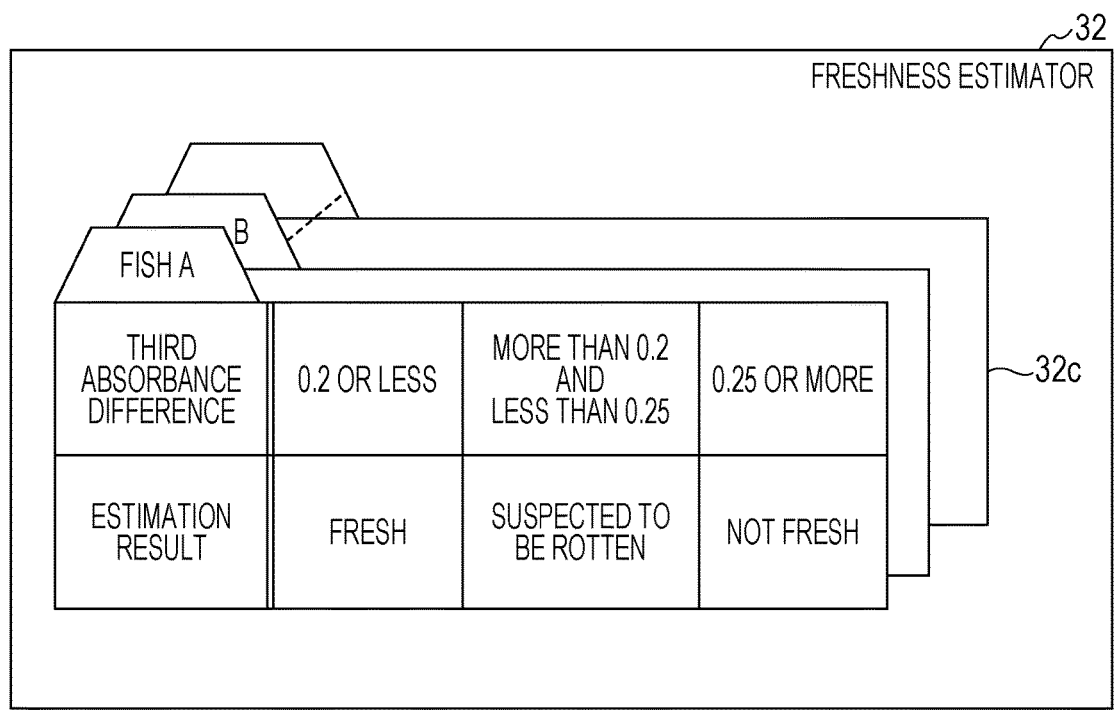
FIG. 11 is a diagram illustrating an example of a threshold table used in the second example of estimating freshness.

In the above-described second example of estimating freshness, the freshness of a fish is estimated by using a pair of thresholds (the threshold A, which is a certain threshold, and the threshold B, which is another threshold), but a plurality of pairs of thresholds may be used. For example, absorbance spectra as those illustrated in FIG. 4 are obtained for individual types and preservation states of fishes, a plurality of pairs of thresholds for the third absorbance difference are determined to distinguish a fresh fish from a non-fresh fish, and the plurality of pairs of thresholds are registered in the threshold table 32c illustrated in FIG. 11 and stored in the freshness estimator 32. Upon receipt of input of information representing the type of a fish as a target for which the freshness is to be estimated and the preservation state of the fish from a user, the freshness estimator 32 refers to the threshold table 32c to read a pair of thresholds corresponding to the received information representing the type and preservation state of the fish, and estimates the freshness of the fish by using the read pair of thresholds. Accordingly, highly-accurate freshness estimation can be performed in consideration of the type and preservation state of the fish.

First Modification Example

A first modification example of the above-described embodiment will be described. In this modification example, an absorbance spectrum is obtained by using a plurality of light sources (a plurality of light sources of monochromatic light) that emit light beams having different wavelengths.

In the above-described embodiment, light emitted from the light source 21 is separated by using the diffraction grating 22 while changing a diffraction angle so as to obtain a continuous absorbance spectrum in the ultraviolet range or from the ultraviolet range to the visible range, and the freshness of a fish is estimated by using the shape of the absorbance spectrum. However, in the above-described first and second examples of estimating freshness, if absorbances in at least two wavelength bands can be obtained, the freshness of a fish can be estimated by calculating the difference or ratio between the absorbances. For example, as in the first example of estimating freshness, the freshness of a fish can be estimated by determining the degree of protrusion of the peak of absorbance relative to a gentle slope portion (a stable portion). Also, for example, as in the second example of estimating freshness, the freshness of a fish can be estimated by determining the difference in absorbance between stable portions in two different wavelength bands (portions where change in absorbance with respect to change in wavelength is relatively small).

In this modification example, a reflection intensity measurer 20a is used instead of the above-described spectrophotometer 20, and thereby absorbances in two wavelengths are easily obtained by using a plurality of light sources that emit light beams of different wavelengths (a plurality of light sources of monochromatic light), so as to estimate the freshness of a fish.

Figure 12:
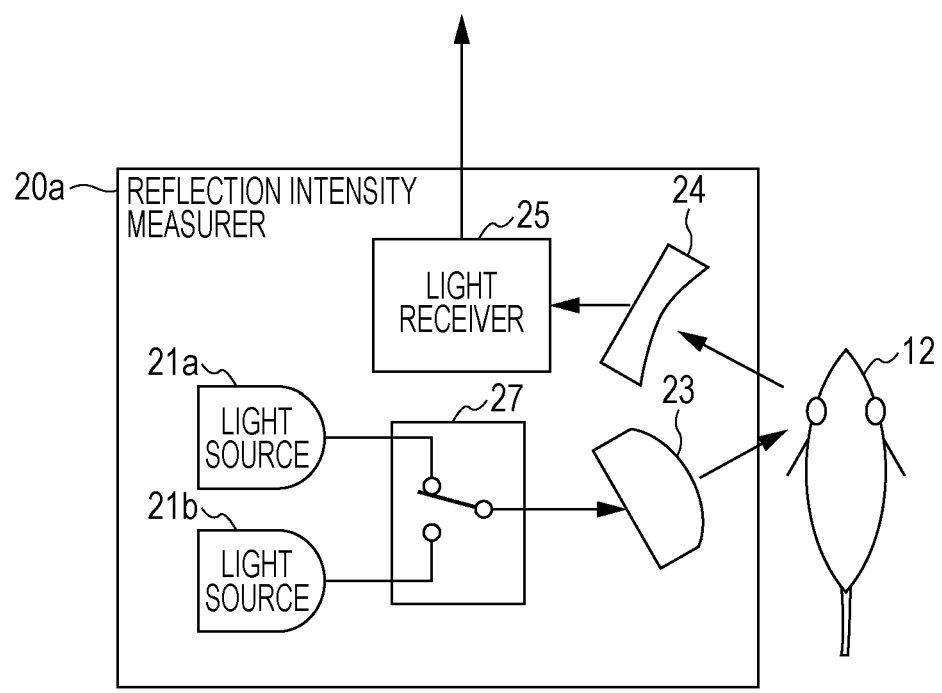
FIG. 12 is a diagram illustrating the configuration of a reflection intensity measurer according to a first modification example of the embodiment of the present disclosure.

FIG. 12 is a diagram illustrating the configuration of the reflection intensity lea surer 20a according to this modification example. The reflection intensity measurer 20a includes light sources 21a and 21b and a selector 27, instead of the light source 21 and the diffraction grating 22 of the spectrophotometer 20 according to the above-described embodiment illustrated in FIG. 1. The reflection intensity measurer 20a is formed by modifying the spectrophotometer 20, and the interface for the terminal apparatus 30 is similar to that of the spectrophotometer 20. Hereinafter, in the reflection intensity measurer 20a, the same elements as those in the above-described spectrophotometer 20 are denoted by the same reference numerals, and the corresponding description will be omitted. A description will be given mainly of a different point.

The two light sources 21a and 21b are a plurality of light sources that emit light beams having different wavelengths (a plurality of light sources of monochromatic light). The selector 27 is a selection switch that selects only one of light beams emitted from the two light sources 21a and 21b and causes the selected light beam to be transmitted. The selector 27 sequentially selects the two light sources 21a and 21b in response to control signals transmitted from a driving device (not illustrated), and thereby sequentially irradiates the eye of the fish 12 with two light beams having different wavelengths.

In the terminal apparatus 30, the absorbance spectrum obtainer 31 receives, from the reflection intensity measurer 20a, information representing the intensity of reflected light or transmitted light generated from the light beams emitted from the two light sources 21a and 21b, and calculates the absorbances in the two wavelengths in accordance with the above-described equation 1, so as to easily calculate an absorbance spectrum. The freshness estimator 32 estimates the freshness of the fish 12 in accordance with the procedure described above in the first and second examples of estimating freshness by using the shape of the absorbance spectrum obtained by the absorbance spectrum obtainer 31, that is, the absorbances in the two wavelengths.

Examples of the combination of the two light sources 21a and 21b are as follows.

(1) First Combination Example

The light source 21a emits light having a narrow band whose intermediate wavelength (peak wavelength) is a certain wavelength between 410 nm and 430 nm, whereas the light source 21b emits light having a narrow band whose intermediate wavelength (peak wavelength) is a certain wavelength between 315 nm to 380 nm. Accordingly, the freshness of a fish can be estimated in the same manner as in the above-described first example of estimating freshness.

(2) Second Combination Example

The light source 21a emits light having a narrow band whose intermediate wavelength (peak wavelength) is a certain wavelength between 410 nm and 430 nm, whereas the light source 21b emits light having a narrow band whose intermediate wavelength (peak wavelength) is a certain wavelength of 450 nm and more (for example, between 450 nm to 600 nm). Accordingly, the freshness of a fish can be estimated in the same manner as in another example of the above-described first example of estimating freshness.

(3) Third Combination Example

The light source 21a emits ultraviolet light having wavelengths in the wavelength band from 315 nm to 380 nm, whereas the light source 21b emits light having a wavelength band of 450 nm and more (for example, visible light having wavelengths in the wavelength band from 450 nm to 600 nm, or infrared light having wavelengths in the wavelength band of up to 1000 nm). Accordingly, the freshness of a fish can be estimated in the same manner as in the above-described second example of estimating freshness.

As described above, according to this modification example, an absorbance spectrum can be easily obtained by irradiating a fish eye with light by switching a plurality of light sources, and a complicated optical system for sweeping the wavelength of light to be applied to the fish eye and separating light into light beams having a plurality of wavelengths is not necessary. Accordingly, the freshness of a fish can be estimated with relatively low cost by using a compact freshness estimation apparatus.

Second Modification Example

Next, a second modification example of the above-described embodiment will be described. In this modification example, a biological fluid in an eyeball of a fish is extracted, the extracted biological fluid is irradiated with light, and the light transmitted through the biological fluid is measured, so as to obtain an absorbance spectrum.

In the above-described embodiment, a fish eye is irradiated with light, and the reflected light thereof is used to estimate the freshness of the fish. In this modification example, a biological fluid in an eyeball is extracted from a fish eye, and an absorbance obtained by irradiating the biological fluid with light (that is, transmitted light) is used to estimate the freshness. Such a method of using transmitted light requires the time and effort for extracting a biological fluid in an eyeball of a fish eye, compared with the method of using reflected light. However, the freshness of the fish can be estimated by using only a biological fluid in an eyeball for which it has been confirmed that the absorbance changes in accordance with lapse of time after death (see the above-described first and second examples of estimating freshness), and thus the freshness of the fish can be estimated with higher accuracy.

Figure 13:
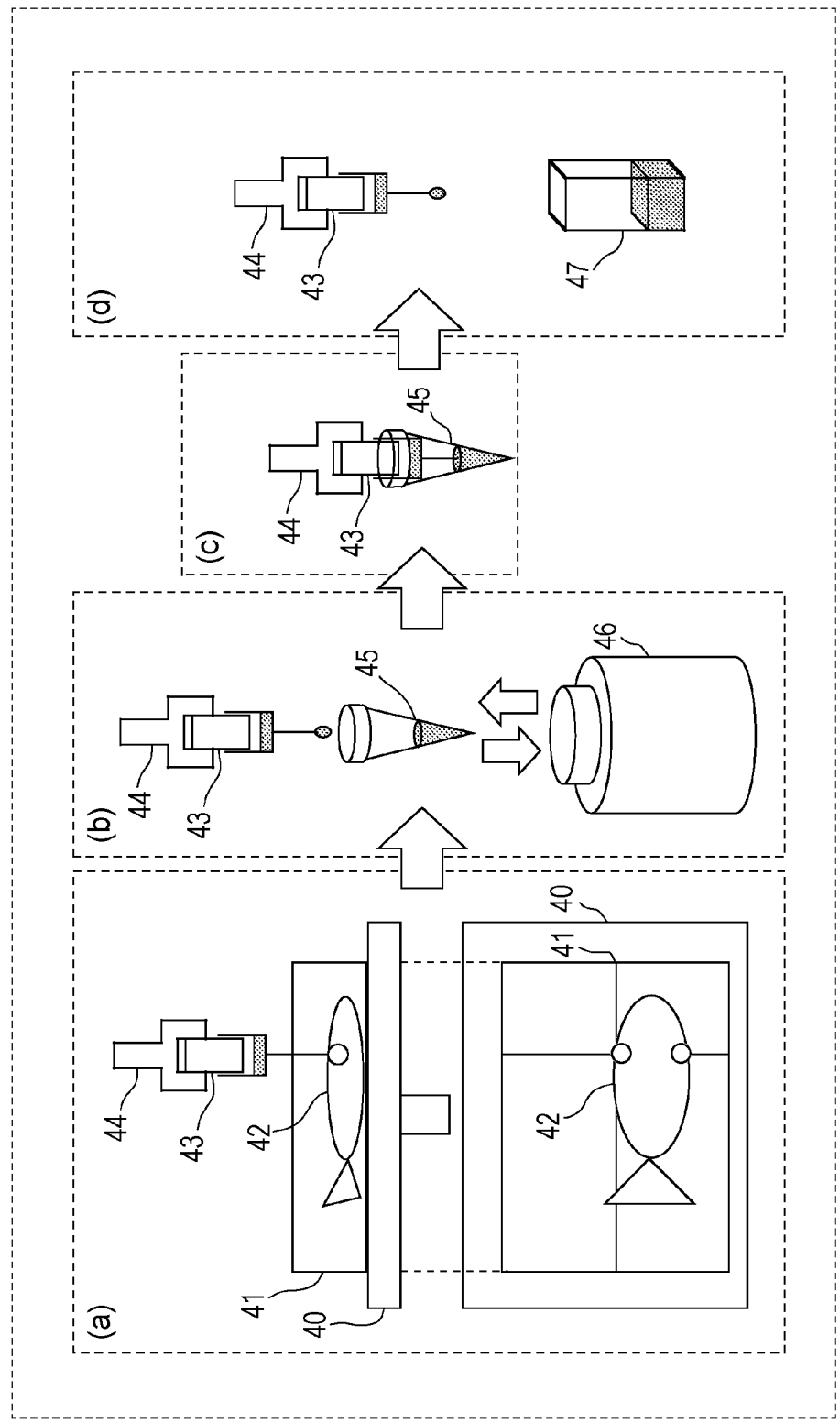
FIG. 13 is a diagram illustrating an apparatus and process procedure of extracting a biological fluid in an eyeball of a fish according to a second modification example of the embodiment of the present disclosure.

Hereinafter, a description will be given of the process of obtaining an absorbance spectrum of a biological fluid in an eyeball. FIG. 13 is a diagram illustrating an apparatus and process procedure for extracting a biological fluid in an eyeball of a fish according to this modification example.

First, a biological fluid in an eyeball is extracted from a fish (part (a) of FIG. 13). As illustrated in part (a) of FIG. 13, a fish 42 is placed on a tray 41. There is a mark indicating a regular position of a fish eye on the tray 41. The fish 42 is placed on the tray 41 such that a fish eye is positioned above the mark. The tray 41 is placed on a table 40 that moves up and down. A syringe 43 is fixed above the table 40. A tip of a needle of the syringe 43 is oriented to the mark indicating the position of a fish eye on the tray 41. After the fish 42 has been placed on the tray 41, the table 40 is raised manually or automatically, and the rise of the table 40 is stopped when the needle of the syringe 43 is inserted into the cornea of the eye of the fish 42. In this case, a mechanism of automatically stopping the table 40 upon detection of a pressure of the cornea may be provided, or the table 40 may be manually stopped. A pressing device 44 fixed to a piston portion of the syringe 43 is raised in a state where the needle of the syringe 43 is in the fish eye, and thereby the biological fluid in the eyeball of the fish 42 is extracted into the syringe 43.

After a certain amount of biological fluid in the eyeball has been extracted ire this way, the biological fluid is centrifugalized by a centrifuge 46 (part (b) of FIG. 13). This process is performed because an absorbance spectrum with less distortion can be obtained by measuring the intensity of light transmitted through a supernatant liquor of the biological fluid. For this purpose, the pressing device 44 fixed to the piston portion of the syringe 43 is pressed down, and thereby the biological fluid in the syringe 43 is injected into a centrifuge tube 45 and is centrifugalized by the centrifuge 46. Regarding the time period of centrifugation, if centrifugation is performed at 5000 rpm for 30 minutes, a target absorbance spectrum of the biological fluid can be obtained, but the rotation speed and the time period are not limited thereto.

As a result of the centrifugation, a supernatant liquor, which is a transparent portion in visible light, is obtained. The supernatant liquor is withdrawn into the syringe 43 that is empty (part (c) of FIG. 13), and is then poured into a cell 47 (part (d) of FIG. 13). The cell 47 is made of a material that allows light to be transmitted therethrough in a wide band from the ultraviolet range to the infrared range, and is desirably made of quartz or the like.

Figure 14:
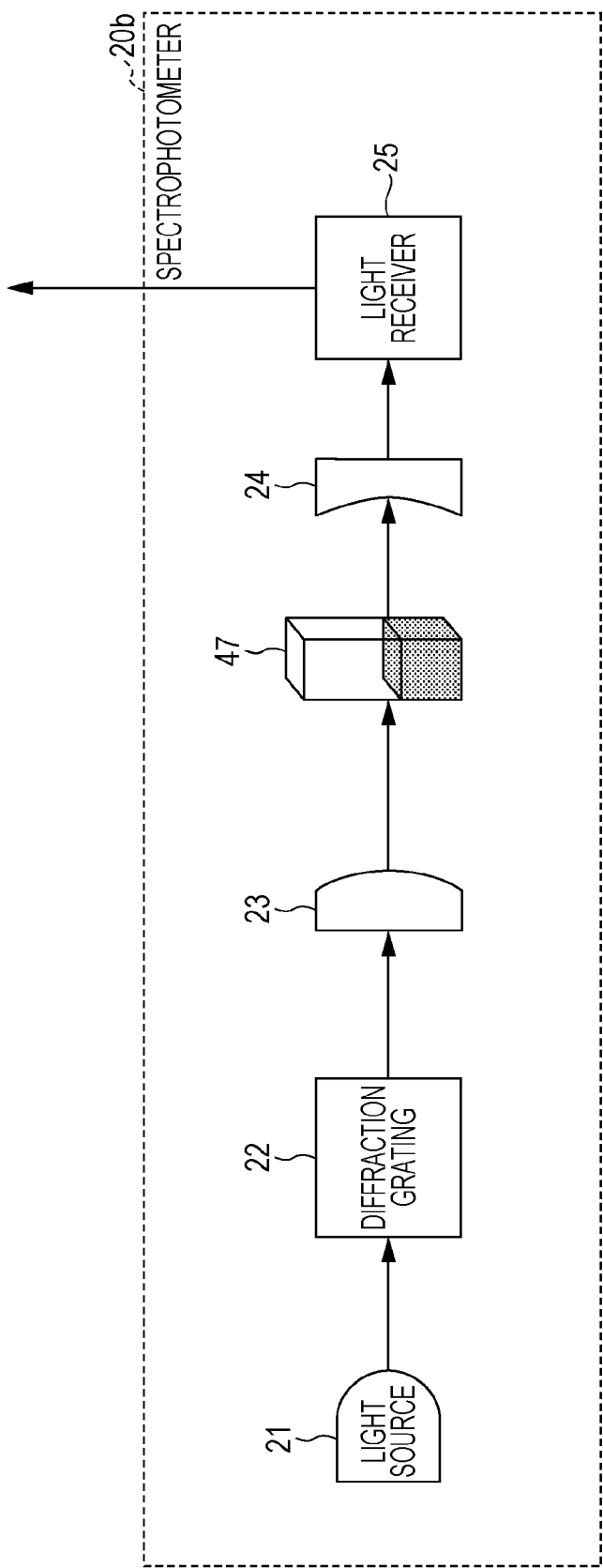
FIG. 14 is a diagram illustrating the configuration of a spectrophotometer according to the second modification example of the embodiment of the present disclosure.

FIG. 14 is a diagram illustrating the configuration of a spectrophotometer 20b according to this modification example. The spectrophotometer 20b includes the same components as those of the spectrophotometer 20 according to the above-described embodiment. However, the condensing lens 24 and the light receiver 25 are provided to detect the intensity of transmitted light, not reflected light. That is, the light emitted from the light source 21 enters the diffraction grating 22. The light that has entered the diffraction grating 22 is separated by the diffraction grating 22, collected by the focus lens 23, and is applied to the cell 47. The cell 47 may be placed on a table whose position adjustable so that the light collected by the focus lens 23 is applied to an appropriate position of the cell 47.

The light that has been transmitted through the cell 47 is condensed by the condensing lens 24 that is behind the cell 47, and enters the light receiver 25. The position of the condensing lens 24 is adjusted so that the light transmitted therethrough is corrected by the light receiver 25.

The processing performed by the terminal apparatus 30 is basically the same as in the above-described embodiment. That is, the absorbance spectrum obtainer 31 receives the intensity of transmitted light from the transmissive spectrophotometer 20b, and calculates absorbances in individual wavelengths in accordance with the above-described equation 1, so as to calculate an absorbance spectrum. The freshness estimator 32 estimates the freshness of the fish 42 by using the shape of the absorbance spectrum calculated by the absorbance spectrum obtainer 31.

Figure 15:
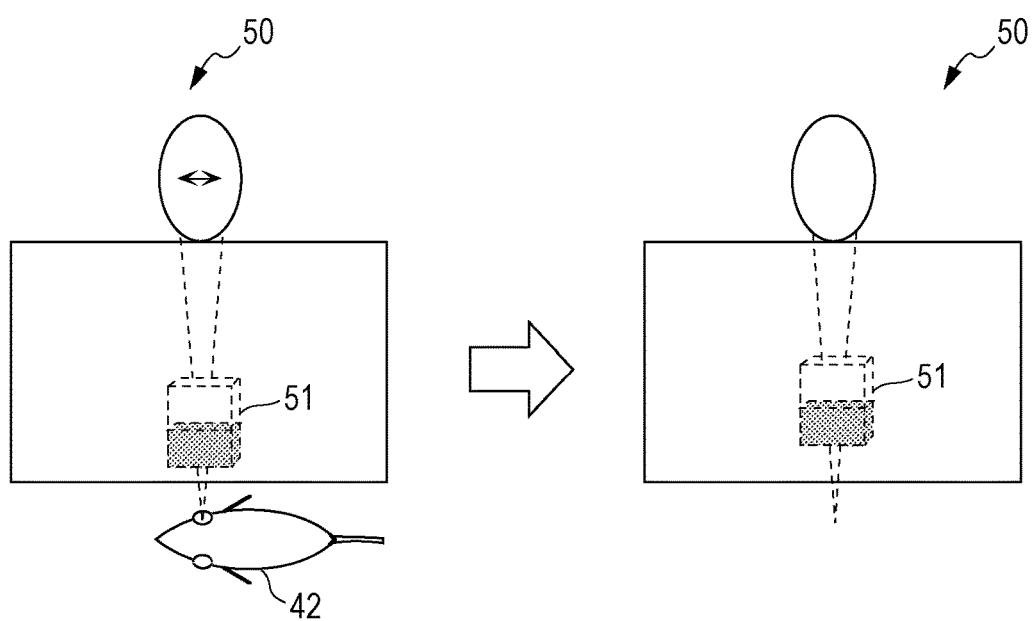
FIG. 15 is a diagram illustrating a dropper-with-liquid-reservoir applicable to the second modification example of the embodiment of the present disclosure.

As described above, according to this modification example, an absorbance spectrum of higher accuracy can be obtained by using the transmission characteristic of light transmitted through a supernatant liquor in a biological fluid in an eyeball of a fish, and accordingly the freshness of the fish can be estimated with higher accuracy, In this modification example, a biological fluid in an eyeball is extracted by using the syringe 43, the extracted biological fluid is centrifugalized by the centrifuge 46 to obtain a supernatant liquor, the supernatant liquor is poured into the cell 47, and thereby an absorbance spectrum is obtained. Alternatively, the biological fluid in the eyeball may be extracted into a dropper-with-liquid-reservoir 50 illustrated in FIG. 15, a spectral characteristic of the biological fluid that is in the dropper-with-liquid-reservoir 50 may be measured by using the spectrophotometer 20b; and thereby an absorbance spectrum may be obtained. FIG. 15 is a diagram illustrating the dropper-with-liquid-reservoir 50 that is applicable to this modification example. As illustrated in FIG. 15, the dropper-with-liquid-reservoir 50 includes a liquid reservoir 51, which stores a sucked biological fluid and which is formed of quartz.

FIG. 16 is a diagram illustrating the configuration of the spectrophotometer 20b in a case where a spectral characteristic is obtained by using the dropper-with-liquid-reservoir 50. FIG. 16 illustrates the configuration of the spectrophotometer 20b in a case where a spectral characteristic of a biological fluid in the dropper-with-liquid-reservoir 50 is obtained by using the spectrophotometer 20b. The spectrophotometer 20b includes the dropper-with-liquid-reservoir 50, which is detachable and which sucks and holds a biological fluid in an eyeball of a fish as a target to be irradiated with light, instead of the cell 47 in the spectrophotometer 20b illustrated in FIG. 14.

With this configuration, a biological fluid in an eyeball of a fish is extracted by using the dropper-with-liquid-reservoir 50, a spectral characteristic is obtained by setting the dropper-with-liquid-reservoir 50 to the spectrophotometer 20b, and the processing described above in the first and second examples of estimating freshness is performed by the terminal apparatus 30. Accordingly, the freshness of the fish can be estimated more easily without using the centrifuge 46.

Also, with such a method using the dropper-with-liquid-reservoir 50, only a biological fluid in an eyeball, for which it has been confirmed that the absorbance changes with lapse of time after death, is used to determine the freshness of a fish, and thus the freshness can be estimated with higher accuracy than in the method of using reflected light from a fish eye, although time and effort are necessary to extract the biological fluid in the eyeball from the fish.

Third Modification Example

Next, a third modification example of the above-described embodiment will be described. In this modification example, absorbance spectra are classified into a class of an absorbance spectrum of a fresh fish and a class of an absorbance spectrum of a non-fresh fish through clustering based on statistical processing, and it is determined which of the classes includes an absorbance spectrum that is similar to the absorbance spectrum of a fish whose freshness is unknown, and thereby the freshness of the fish is estimated.

In the above-described embodiment, the relationship between the shapes of absorbance spectra of a fish eye and the freshness of a fish is analyzed to obtain a threshold, and the freshness of a target fish hose freshness is unknown is estimated by using the threshold and the shape of the absorbance spectrum of the target fish. However, the inventors have found that clustering (multivariate analysis) based on statistical processing performed on various absorbance spectra of fishes enables automatic classification into a class of an absorbance spectrum of a fresh fish and a class of an absorbance spectrum of a non-fresh fish, even if the relationship between the shapes of absorbance spectra and the freshness of a fish is not analyzed. Therefore, it has been determined that the freshness of a target fish whose freshness is unknown can be easily estimated in accordance with the absorbance spectrum of the target fish by using the classification result.

Figure 17A:
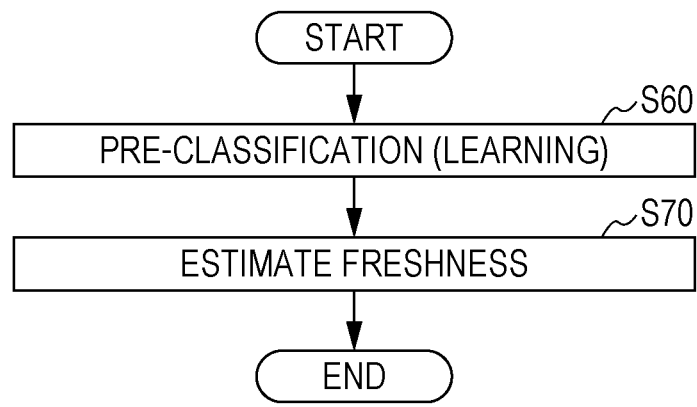
FIG. 17A is a flowchart illustrating a basic operation of a freshness estimation apparatus according to a third modification example of the embodiment of the present disclosure.

FIG. 17A is a flowchart illustrating a basic operation of the freshness estimation apparatus (freshness estimation method for a fish) according to this modification example. The freshness estimation method is roughly constituted by two steps. That is, pre-classification into a class of an absorbance spectrum of a fresh fish and a class of an absorbance spectrum of a non-fresh fish (learning) is performed (S60). Subsequently, the freshness of a target fish whose freshness is unknown is estimated in accordance with the absorbance spectrum of the target fish by using the classification result (S70).

Figure 17B:
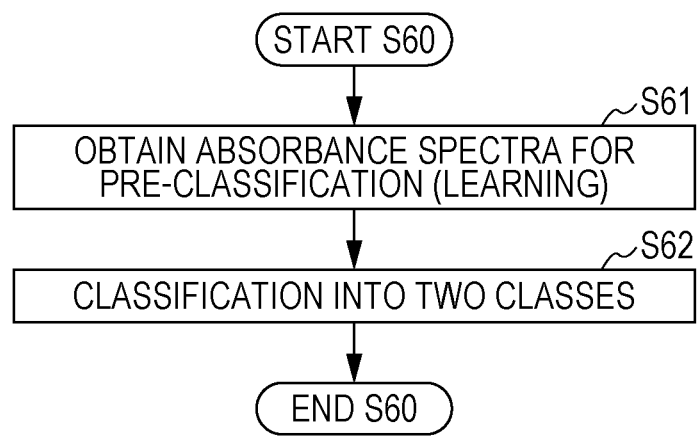
FIG. 17B is a flowchart illustrating a specific procedure of step S60 (pre-classification) in FIG. 17A.

FIG. 17B is a flowchart illustrating a specific procedure of step S60 (pre-classification) in FIG. 17A. The absorbance spectrum obtainer 31 of the terminal apparatus 30 obtains, by using the spectrophotometer 20, absorbance spectra (for example, absorbance spectra in a wavelength band from 315 nm to 600 nm) for a plurality of fishes including a fresh fish and a non-fresh fish for pre-classification (learning) (S61). Subsequently, the freshness estimator 32 of the terminal apparatus 30 classifies the plurality of absorbance spectra that have been obtained for pre-classification (learning) by the absorbance spectrum obtainer 31 into two classes through clustering (multivariate analysis) based on statistical processing (S62). In this classification, teaching indicating which absorbance spectrum corresponds to a fresh fish and which absorbance spectrum corresponds to a non-fresh fish is not necessary. The clustering (multivariate analysis) based on statistical processing is performed so that all the absorbance spectra as classification targets are classified into two classes with a high degree of separation. Accordingly, the absorbance spectra are automatically classified into a class of an absorbance spectrum of a fresh fish and a class of an absorbance spectrum of a non-fresh fish, as described above.

Figure 17C:
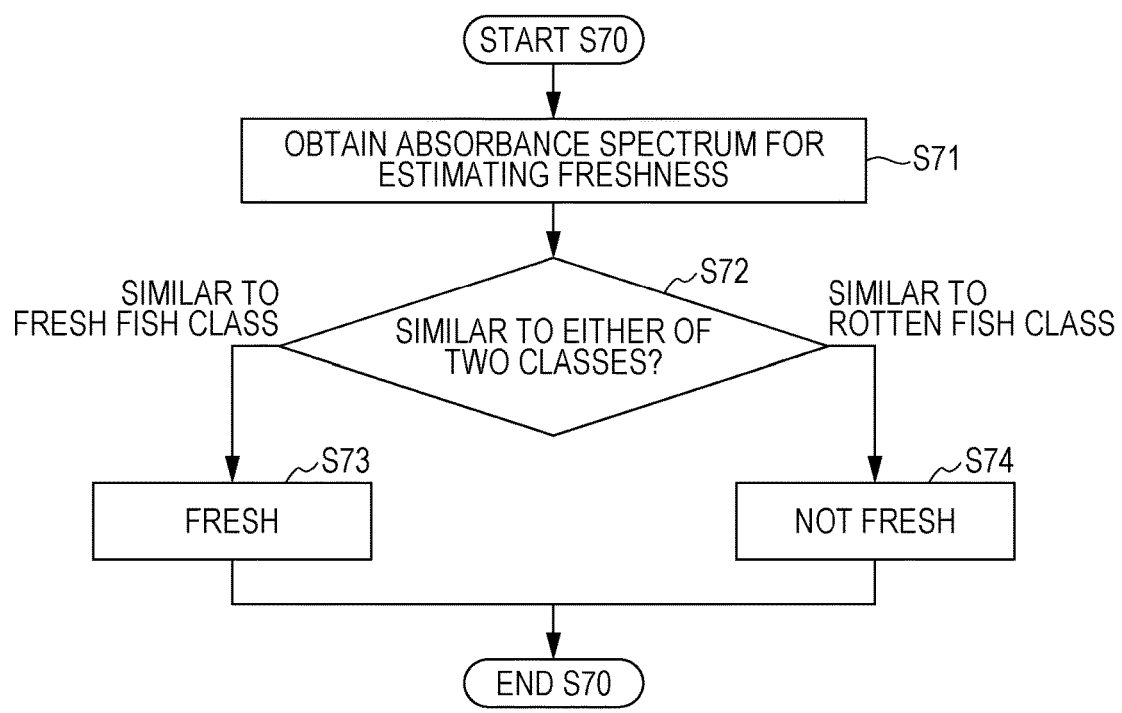
FIG. 17C is a flowchart illustrating a specific procedure of step S70 (freshness estimation) in FIG. 17A.

FIG. 17C is a flowchart illustrating a specific procedure of step 370 (freshness estimation) in FIG. 17A. The absorbance spectrum obtainer 31 obtains, by using the spectrophotometer 20, an absorbance spectrum (for example, an absorbance spectrum in a wavelength band from 315 nm to 600 nm) of a target fish for which the freshness is to be estimated (S71). Subsequently, the freshness estimator 32 determines which of the two classes obtained in the above-described classification (step 360 in FIG. 17A and steps 361 and S62 in FIG. 17B) includes an absorbance spectrum that is similar to the absorbance spectrum obtained for estimating freshness by the absorbance spectrum obtainer 31 (S72), and estimates the freshness of the fish in accordance with the determination result (S73 and S74). Specifically, if the absorbance spectrum obtained for estimating freshness is similar to the absorbance spectrum of a fresh fish ("similar to fresh fish class" in S72), it is determined that the fish is fresh (S73). On the other hand, if the absorbance spectrum obtained for estimating freshness is similar to the absorbance spectrum of a non-fresh fish ("similar to rotten fish class" in S72), it is determined that the fish is not fresh (S74). In this way, the freshness of the fish can be estimated by using the absorbance spectrum of the fish whose freshness is unknown.

The similarity may be determined in accordance with the distance between multidimensional vectors by regarding an absorbance spectrum as a multidimensional vector. More specifically, the similarity may be determined by considering which is of the following two distances is shorter: the distance between an average (absorbance spectrum) of absorbance spectra classified into the fresh fish class and the absorbance spectrum of a fish whose freshness is unknown, and the distance between an average (absorbance spectrum) of absorbance spectra classified into the non-fresh fish class and the absorbance spectrum of a fish whose freshness is unknown.

Figure 18:
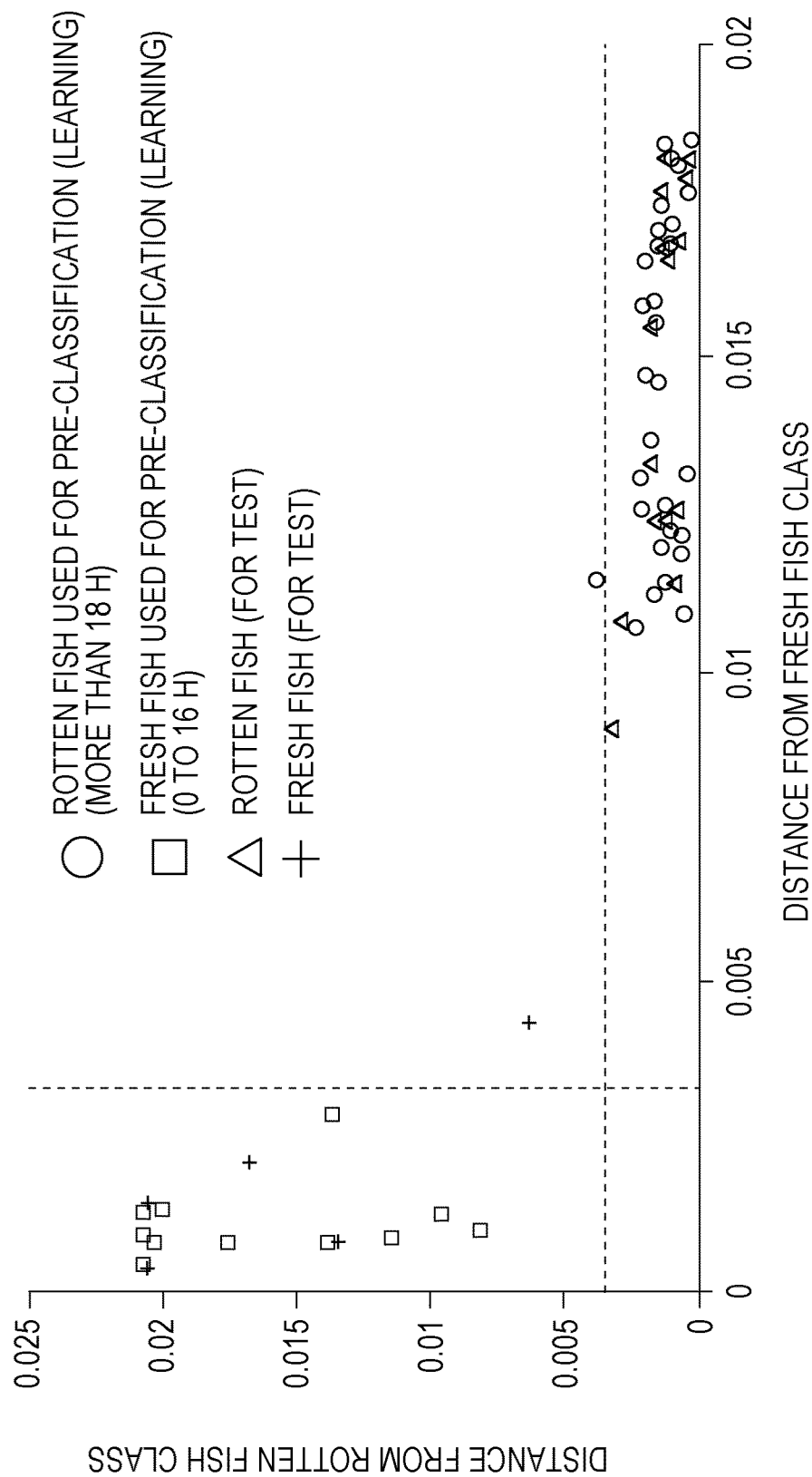
FIG. 18 is a plot illustrating a result of freshness estimation according to the third modification example of the embodiment of the present disclosure.

FIG. 18 is a diagram illustrating a result of freshness estimation according to this modification example. FIG. 18 illustrates a plot of distances between two classes created by using a soft independent modeling of class analogy (SIMCA) method, which is a method for multivariate analysis, and absorbance spectra obtained from fish eyes that are not used for learning of classes. The horizontal axis indicates the distance from the fresh fish class, and the vertical axis indicates the distance from the non-fresh fish class (rotten fish class). In this plot, a circle represents data of a fish that has been dead for more than 18 hours (rotten fish) used for pre-classification (learning), a square represents data of a fish that has been dead for no longer than 16 hours (fresh fish) used for pre-classification (learning), a triangle represents data of a fish that has been dead for more than 18 hours (rotten fish) used for a test, and a cross represents data of a fish that has been dead for no longer than 16 hours (fresh fish) used for a test. A distance from a class means a distance from an average (absorbance spectrum) of absorbance spectra belonging to the class.

For pre-classification (learning), absorbance spectra of eight fish eyes are calculated every hour from the time 1 hour after death to the time 96 hours after death, and the calculated absorbance spectra are used. The obtained absorbance spectra are classified into two classes by using the SIMCA method. The SIMCA method is a method for multivariate analysis (see http://www.gls.co.jp/glsoft/chemomet/chemometo/simca/simca.html). The clustering based on statistical processing (multivariate analysis) is not limited to the SIMCA method, and another clustering method may be used.

As can be understood from the circles and squares in the plot in FIG. 18, the absorbance spectra used for a test are classified, using the SIMCA method, into a class corresponding to a fish of a high degree of freshness, constituted by absorbance spectra of fishes that have been dead for 1 to 16 hours, and a class corresponding to a fish of a low degree of freshness, constituted by absorbance spectra of fishes that have been dead for more than 18 hours.

Regarding the absorbance spectra obtained in accordance with lapse of time from eight eyes of fishes that have not been used for pre-classification (learning), the distance from the already classified two classes is calculated. As a result, the absorbance spectrum corresponding to a fish of a high degree of freshness (a fish that has been dead for no longer than 16 hours) has a short distance with respect to a high freshness class, and the absorbance spectrum corresponding to a fish of a low degree of freshness (a fish that has been dead for more than 18 hours) has a short distance with respect to a low freshness class. The percentage of correct estimation of freshness under this method is high of 90% or more. The reason for such highly accurate estimation of freshness may be that the characteristic of an absorbance spectrum of a biological fluid in an eyeball of a fish differs between a fish whose freshness is high and a fish whose freshness is low.

As described above, according to this modification example, absorbance spectra are classified into a class of a fresh fish and a class of a non-fresh fish through clustering based on statistical processing, and it is determined which of the two classes includes an absorbance spectrum that is similar to the absorbance spectrum of a target fish whose freshness is unknown, and accordingly the freshness of the target fish is estimated. Accordingly, the freshness of the fish is estimated with high accuracy without using complicated determination processing, by using a characteristic in which absorbance spectra of fish eyes having a wavelength band from 315 nm to 450 nm are automatically classified into two classes, a fresh fish class and a non-fresh fish class.

Fourth Modification Example

Next, a fourth modification example of the above-described embodiment will be described. In this modification example, an absorbance is obtained by using a single light source (a light source of monochromatic light) that emits light having one wavelength in a certain wavelength band (for example, from 410 nm to 430 nm) in which a peak of absorbance appears in the above-described absorbance spectrum (see FIG. 4). In this way, the freshness of a fish can be estimated by using an absorbance in one wavelength in a case where some conditions are set, such as the type of a fish as a target for which the freshness is to be estimated and the humidity around the fish.

In this modification example, a reflection intensity measurer 20c is used instead of the reflection intensity measurer 20a according to the second modification example, and thereby an absorbance is easily obtained by using a single light source of monochromatic light and the absorbance is compared with a predetermined threshold, so as to estimate the freshness of a fish. For this purpose, a terminal apparatus 30a for estimating the freshness of a fish by using one absorbance is used, instead of the terminal apparatus 30 that uses an absorbance spectrum. If the absorbance is smaller than the threshold, it can be estimated that the fish is fresh. If the absorbance is equal to or larger than the threshold, it can be estimated that the fish is not fresh. The threshold may be determined through an experiment that is performed in advance for each type of fish. For example, as in the case illustrated in FIG. 4, the threshold may be determined by regarding, as a boundary between fresh and non-fresh, the absorbance obtained at the time when 18 hours have elapsed from death of the fish. Specifically, for example, 0.3±0.05 may be used as a threshold.

Also, an absorbance may be measured in a state where a fish is wrapped by a wrapping film for food and the humidity is kept at about 90%, in order to keep the humidity around the fish constant.

Figure 19:
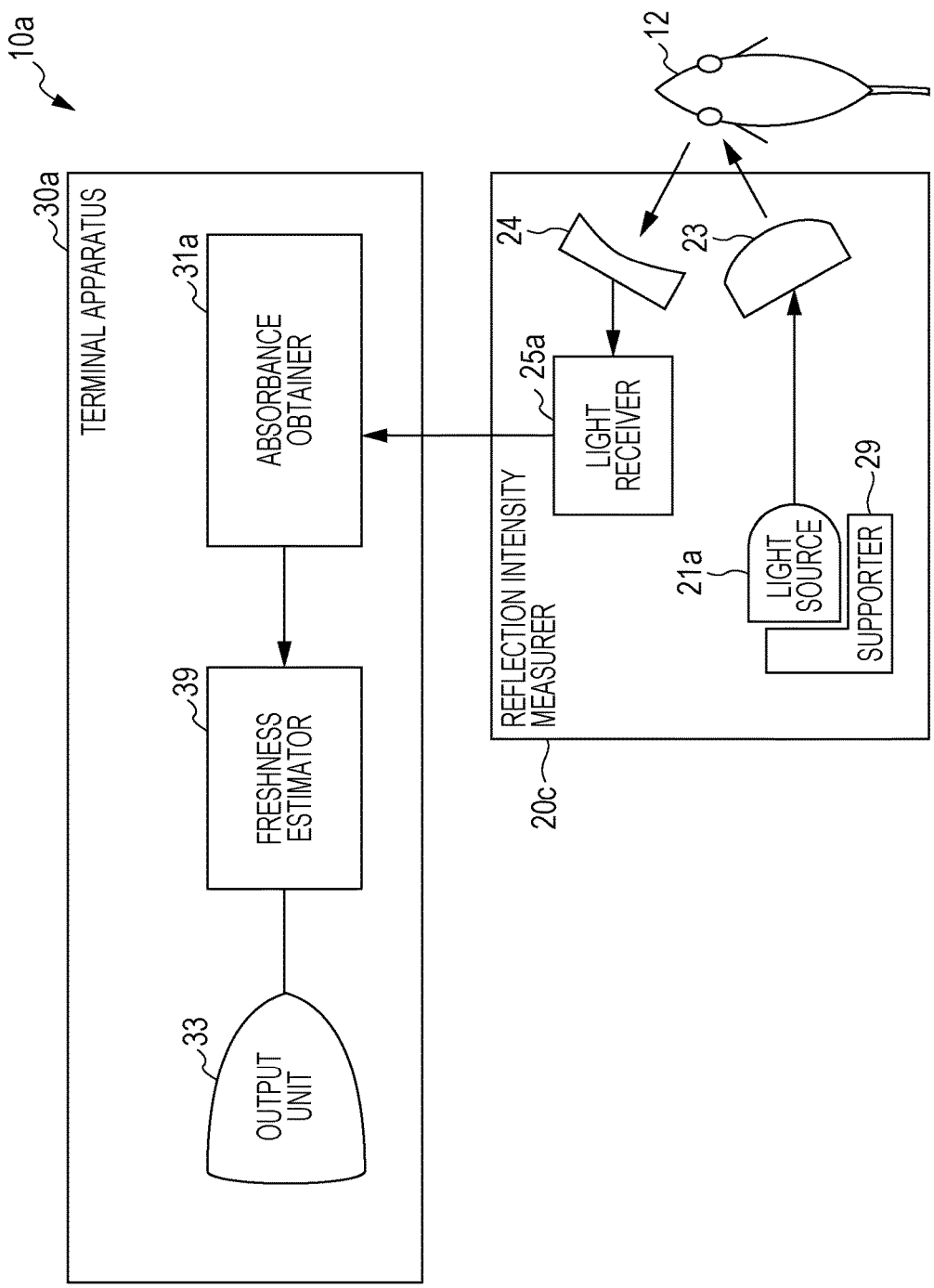
FIG. 19 is a diagram illustrating the configuration of a freshness estimation apparatus according to a fourth modification example of the embodiment of the present disclosure.

FIG. 19 is a diagram illustrating the configuration of a freshness estimation apparatus 10a (the terminal apparatus 30a and the reflection intensity measurer 20c) according to this modification example. The terminal apparatus 30a includes an absorbance obtainer 31a instead of the absorbance spectrum obtainer 31 of the terminal apparatus 30 illustrated in FIG. 1, and includes a freshness estimator 39 that estimates the freshness of a fish by comparing one absorbance with a threshold, instead of the freshness estimator 32. The reflection intensity measurer 20c is formed by removing the light source 21b and the selector 27 of the reflection intensity measurer 20a illustrated in FIG. 12 and adding a supporter 29. Hereinafter, in the terminal apparatus 30a and the reflection intensity measurer 20c, the same elements as those of the terminal apparatus 30 and the reflection intensity measurer 20a are denoted by the same reference numerals and the corresponding description is omitted. Hereinafter, a description will be given mainly of a different point.

The light source 21a is a light source that emits monochromatic light having one wavelength in a wavelength band from 410 nm to 430 nm. The supporter 29 is a mechanism for supporting the light source 21a so that the optical axis of the light source 21a is movable within a certain range.

A light receiver 25a is a sensor that detects the intensity of reflected light that has entered through the condensing lens 24 (converts light into an electric signal), and is, for example, a photomultiplier tube, a photodiode, or the like.

The reflection intensity measurer 20c performs measurement a plurality of times by changing, using the supporter 29, a position where the light emitted from the light source 21a is applied to a fish eye through the focus lens 23. The light receiver 25a receives reflected light from the fish eye via the condensing lens 24, and transmits, to the terminal apparatus 30a, the maximum intensity of reflected light among intensities detected in a plurality of measurements.

The absorbance obtainer 31a of the terminal apparatus 30a is a processor that obtains an absorbance by irradiating a fish eye with light in a wavelength band from 410 nm to 430 nm, and includes a communication interface that obtains the intensity of reflected light or transmitted light from the reflection intensity measurer 20c and an arithmetic processor that calculates an absorbance in accordance with the above-described equation 1.

The freshness estimator 39 is a processor that estimates the freshness of the fish 12 by using an absorbance obtained by the absorbance obtainer 31a (that executes a freshness estimation method for a fish), and includes an arithmetic processor or the like.

In the terminal apparatus 30a, the absorbance obtainer 31a receives, from the reflection intensity measurer 20c, the intensity of reflected light or transmitted light generated from the light emitted by the light source 21a, and calculates an absorbance in accordance with the above-described equation 1. Subsequently, the freshness estimator 39 compares the absorbance with a threshold to estimate whether or not the fish is fresh, and the output unit 33 outputs the estimation result. For example, the freshness estimator 39 determines (estimates) that the fish is fresh if the absorbance is smaller than the threshold, and determines (estimates) that the fish is rotten if the absorbance is equal to or larger than the threshold.

As described above, according to this modification example, the freshness of a fish can be estimated by using a simple configuration of irradiating a fish eye with light by using a single light source. Even if the optical axis of the light source 21a is not changed by the supporter 29 (even if the supporter 29 is not provided), the freshness of a fish can be estimated with a certain degree of accuracy by performing measurement a plurality of times by changing the positional relationship between the eye of the fish 12 and the optical axis of light emitted from the reflection intensity measurer 20c and by using an average value or maximum value of absorbance.

The freshness estimation method and the freshness estimation apparatus according to one or a plurality of modes of the present disclosure have been described based on an embodiment and its modification examples. The present disclosure is not limited by the embodiment and modification examples. Various modifications of the embodiment and modification examples conceived by those skilled in the art, and a configuration formed by a combination of elements in different embodiments or modification examples may be included in the scope of one or a plurality of modes of the present disclosure without deviating from the gist of the present disclosure.

For example, in the above-described embodiment and modification examples, the freshness estimator 32 estimates whether a fish is fresh or not fresh, or whether a fish is fresh, is suspected to be rotten, or is not fresh. However, the estimation is not limited to such estimation in two or three stages. The freshness estimator 32 may estimate the probability of a fish being fresh in accordance with the difference between a threshold and the difference or ratio between absorbances in an absorbance spectrum, or in accordance with a distance between an absorbance spectrum of a fish whose freshness is unknown and a fresh fish class.

In the above-described embodiment, a plurality of examples of estimating freshness have been described. In the above-described modification examples, an example of estimating freshness by using clustering has been described. These examples of estimating freshness may be selectively used, or may be used in combination. The example of estimation to be used may be determined by a presetting in the terminal apparatus 30, or may be determined through a dialog between the terminal apparatus 30 and a user each time.

The freshness estimation method for a fish according to the above-described embodiment may be implemented by the following program. The program causes a computer to perform processing that includes obtaining an absorbance spectrum that is obtained by irradiating an eye of a fish with light having all or part of a wavelength band from 315 nm to 450 nm, and estimating freshness of the fish by using a shape of the obtained absorbance spectrum. This program enables a freshness estimation method for a fish with which the freshness of an entire fish can be objectively estimated with higher accuracy.

In the above-described embodiment, light having a wavelength band from 315 nm to 450 nm is used, and wavelengths in the range from 315 nm to 380 nm, the range from 410 nm to 430 nm, 600 nm, 1000 nm, and so forth are used. Actually, however, a margin (error) of about ±5 nm to be considered for the range of a wavelength band and individual wavelengths in view of an influence of an individual difference of a fish, a measurement environment, and so forth. Thus, the range of a wavelength band that is to be actually used may be, for example, 315 nm±5 nm to 450 m±5 nm, 315 nm±5 nm to 380 nm±5 m, 410 nm±5 nm to 430 nm±5 nm, and so forth.

In the above-described embodiment, the main processors of the freshness estimation apparatus 10 (the absorbance spectrum obtainer 31 and the freshness estimator 32) are constituted by a single terminal apparatus 30, and the main processors of the freshness estimation apparatus 10a (the absorbance obtainer 31a and the freshness estimator 39) are constituted by a single terminal apparatus 30a. Alternatively, these processors may be constituted by a plurality of terminal apparatuses and computers. That is, a plurality of terminal apparatuses and computers may communicate with one another to perform the processing of estimating the freshness of a fish in cooperation with one another.

An embodiment of the present disclosure is applicable to a freshness estimation method and freshness estimation apparatus for determining the freshness of a fish in a non-contact and non-invasive method in a short time in a site where fishes have been cached or fishes are being circulated, and thereby providing a system for efficiently ensuring the safety of food.

What is claimed is:
1. A freshness estimation method comprising:
emitting, with at least one light source, light having all or part of a wavelength band from 315 nm to 450 nm, and irradiating an eye of a fish with the light;
detecting, with a light sensor, an intensity of light reflected from the eye of the fish;
calculating, with a processor, an absorbance spectrum based on the intensity of light detected by the light sensor;
calculating, with the processor, an absorbance difference by subtracting an absorbance in a certain wavelength in a wavelength band from 315 nm to 380 nm from a peak value of absorbance in a wavelength band from 410 nm to 430 nm;
determining, with the processor, whether the calculated absorbance difference is smaller than a predetermined threshold; and
outputting an indication, via at least one of a visual output device or sound output device, when the calculated absorbance difference is smaller than the predetermined threshold, thereby indicating that the fish is fresh.
2. The freshness estimation method according to claim 1, comprising emitting the light with a a plurality of light sources that emit a plurality of pieces of light having different wavelengths and the light includes the plurality of pieces of light.

3. A freshness estimation method comprising:
emitting, with at least one light source, light having all or part of a wavelength band from 315 nm to 450 nm, and irradiating an eye of a fish with the light;
detecting, with a light sensor, an intensity of light reflected from the eye of the fish;
calculating, with a processor, an absorbance spectrum based on the intensity of light detected by the light sensor;
calculating, with the processor, an absorbance difference by subtracting an absorbance in a certain wavelength in a wavelength band of 450 nm and more from a peak value of absorbance in a wavelength band from 410 nm to 430 nm;
determining, with the processor, whether the calculated absorbance difference is smaller than a predetermined threshold; and
outputting an indication, via at least one of a visual output device or sound output device, when the calculated absorbance difference is smaller than the predetermined threshold, thereby indicating that the fish is fresh.

4. A freshness estimation method comprising:
emitting, with at least one light source, light having a wavelength band of 450 nm and more in addition to a wavelength band from 315 nm to 380 nm, and irradiating an eye of a fish with the light;
detecting, with a light sensor, an intensity of light reflected from the eye of the fish;
calculating, with a processor, an absorbance spectrum based on the intensity of light detected by the light sensor;
calculating, with the processor, an absorbance difference, which is a difference between an absorbance in the wavelength band from 315 nm to 380 nm in the absorbance spectrum and an absorbance in the wavelength band of 450 nm and more in the absorbance spectrum;
determining, with the processor, whether the calculated absorbance difference is equal to or smaller than a predetermined threshold; and
outputting a freshness indication, via at least one of a visual output device or sound output device, when the calculated absorbance difference is equal to or smaller than the predetermined threshold, thereby indicating that the fish is fresh.

5. The freshness estimation method according to claim 4, further comprising:
outputting an unfresh indication, when the calculated absorbance difference is equal to or larger than another threshold that is larger than the predetermined threshold.

6. A freshness estimation method comprising:
extracting a biological fluid in an eyeball of the fish;
emitting, with at least one light source, light having all or part of a wavelength band from 315 nm to 450 nm, and irradiating the extracted biological fluid with the light;
detecting, with a light sensor, an intensity of light that has been transmitted through the biological fluid;
calculating, with a processor, an absorbance spectrum based on the intensity of light detected by the light sensor;
calculating, with the processor, an absorbance difference by subtracting an absorbance in a certain wavelength in a wavelength band from 315 nm to 380 nm from a peak value of absorbance in a wavelength band from 410 nm to 430 nm;
determining, with the processor, whether the calculated absorbance difference is smaller than a predetermined threshold; and
outputting an indication, via at least one of a visual output device or sound output device, when the calculated absorbance difference is smaller than the predetermined threshold, thereby indicating that the fish is fresh.

7. A freshness estimation method comprising:
emitting, with at least one light source, light having all or part of a wavelength band from 315 nm to 450 nm, and irradiating an eye of a plural fishes with the light, the plural fished including fresh fish and non-fresh fish;
detecting, with a light sensor, an intensity of light reflected from the eyes of the respective fishes;
calculating, with a processor, for classification, a plurality of absorbance spectra for the plural fishes, respectively, based on the intensity of light detected by the light sensor;
calculating, with the processor, for freshness estimation, an absorbance spectrum for a fish as a target for which freshness is to be estimated;
classifying, with the processor, the plurality of absorbance spectra obtained for classification into two classes, and
determining, with the processor, which of the two classes includes an absorbance spectrum that is similar to the absorbance spectrum obtained for freshness estimation; and
outputting an indication, via at least one of a visual output device or sound output device, based on a result of the determination.

8. A non-transitory computer-readable recording medium storing a program for causing an apparatus including a processor to execute processing, the processing comprising:
emitting, with at least one light source, light having all or part of a wavelength band from 315 nm to 450 nm, and irradiating an eye of a fish with the light;
detecting, with a light sensor, an intensity of light reflected from the eye of the fish;
calculating, with a processor, an absorbance spectrum based on the intensity of light detected by the light sensor;
calculating, with the processor, an absorbance difference by subtracting an absorbance in a certain wavelength in a wavelength band from 315 nm to 380 nm from a peak value of absorbance in a wavelength band from 410 nm to 430 nm;
determining, with the processor, whether the calculated absorbance difference is smaller than a predetermined threshold; and
outputting an indication, via at least one of a visual output device or sound output device, when the calculated absorbance difference is smaller than the predetermined threshold, thereby indicating that the fish is fresh.

9. A freshness estimation apparatus comprising:
an absorbance spectrum obtainer that obtains an absorbance spectrum that is obtained by irradiating an eye of a fish with light having all or part of a wavelength band from 315 nm to 450 nm; and
a processor that:
calculates an absorbance difference by subtracting an absorbance in a certain wavelength in a wavelength band from 315 nm to 380 nm from a peak value of absorbance in a wavelength band from 410 nm to 430 nm;

determines whether the calculated absorbance difference is smaller than a predetermined threshold; and outputs an indication, via at least one of a visual output device or sound output device, when the calculated absorbance difference is smaller than the predetermined threshold, thereby indicating that the fish is fresh.

10. The freshness estimation apparatus according to claim 9, further comprising:

a spectrophotometer that detects an intensity of light reflected by the eye or light transmitted through the eye, wherein the absorbance spectrum obtainer obtains the absorbance spectrum by calculating the absorbance spectrum by using the intensity detected by the spectrophotometer.

11. The freshness estimation apparatus according to claim 9, further comprising:

a reflection intensity measurer that detects intensities of a plurality of pieces of resulting light reflected by the eye, the light including a plurality of light having different wavelengths, a plurality of light sources emitting the plurality of pieces of light, wherein the absorbance spectrum obtainer obtains the absorbance spectrum by calculating the absorbance spectrum by using the intensities detected by the reflection intensity measurer.

12. A freshness estimation apparatus comprising:

an absorbance spectrum obtainer that obtains an absorbance spectrum that is obtained by irradiating an eye of a fish with light having all or part of a wavelength band from 315 nm to 450 nm; and a freshness estimator that estimates freshness of the fish, by using a shape of the obtained absorbance spectrum; and a spectrophotometer that detects an intensity of light reflected by the eye or light transmitted through the eye, wherein the absorbance spectrum obtainer obtains the absorbance spectrum by calculating the absorbance spectrum by using the intensity detected by the spectrophotometer, wherein the spectrophotometer includes a detachable dropper for sucking a biological fluid in an eyeball of the fish and for holding the biological fluid, and wherein the dropper includes a liquid reservoir that is made of quartz and that is used for storing the biological fluid that has been sucked.

* * * * *